US011045327B2

(12) United States Patent
Nichols et al.

(10) Patent No.: US 11,045,327 B2
(45) Date of Patent: Jun. 29, 2021

(54) ADJUSTABLE INTERBODY FUSION DEVICES AND METHODS OF USE

(71) Applicant: BIOSPINE, LLC, Columbia City, IN (US)

(72) Inventors: Ross R. Nichols, North Webster, IN (US); Daniel Refai, Atlanta, GA (US); Brian G. Emerick, Columbia City, IN (US); Heidi Stamets, Monroeville, IN (US)

(73) Assignee: BIOSPINE, LLC, Columbia City, IN (US)

( * ) Notice: Subject to any disclaimer, the term of this patent is extended or adjusted under 35 U.S.C. 154(b) by 127 days.

(21) Appl. No.: 16/401,852

(22) Filed: May 2, 2019

(65) Prior Publication Data

US 2019/0254839 A1 Aug. 22, 2019

Related U.S. Application Data

(63) Continuation of application No. 15/991,460, filed on May 29, 2018, now Pat. No. 10,278,832, which is a
(Continued)

(51) Int. Cl.
*A61F 2/44* (2006.01)
*A61F 2/30* (2006.01)
(Continued)

(52) U.S. Cl.
CPC ........ *A61F 2/4455* (2013.01); *A61F 2/30767* (2013.01); *A61F 2/442* (2013.01);
(Continued)

(58) Field of Classification Search
CPC combination set(s) only.
See application file for complete search history.

(56) References Cited

U.S. PATENT DOCUMENTS

| 4,759,769 A | | 7/1988 | Hedman | |
|---|---|---|---|---|
| 5,522,899 A | * | 6/1996 | Michelson | ............. A61F 2/442 606/279 |

(Continued)

FOREIGN PATENT DOCUMENTS

| EP | 2226039 | 9/2010 |
|---|---|---|
| WO | 2009064787 | 5/2009 |

(Continued)

OTHER PUBLICATIONS

Extended European Search Report issued for European Application No. 14798042.9 dated Dec. 20, 2016.
(Continued)

*Primary Examiner* — Lynnsy M Summitt
(74) *Attorney, Agent, or Firm* — Heslin Rothenberg Farley & Mesiti P.C.; Jacquelyn A. Graff, Esq.

(57) ABSTRACT

Interbody fusion devices, insertion tools, methods for assembling an interbody fusion device, and methods for inserting a medical device between two vertebral bodies are disclosed. The interbody fusion device includes a base member, a top member, and at least one movement mechanism. The base member includes at least one of a pivotal cylinder and a hinge channel. The top member includes at least one of a pivot cylinder and a hinge channel. The at least one pivot cylinder of the base member engages the at least one hinge channel of the top member and the at least one pivot cylinder of the top member engages the at least one hinge channel of the base member. The at least one movement mechanism engages the top member and the base member. Also disclosed are a vertebral spacer device and an interbody spacer system including an insertion tool and an interbody fusion device.

20 Claims, 25 Drawing Sheets

Related U.S. Application Data continuation of application No. 14/890,837, filed as application No. PCT/US2014/037884 on May 13, 2014, now Pat. No. 9,980,825.

(60) Provisional application No. 61/822,620, filed on May 13, 2013.

(51) Int. Cl.
*A61F 2/46* (2006.01)
*A61F 2/28* (2006.01)

(52) U.S. Cl.
CPC ............ *A61F 2/447* (2013.01); *A61F 2/4425* (2013.01); *A61F 2/4611* (2013.01); *A61F 2002/2835* (2013.01); *A61F 2002/3039* (2013.01); *A61F 2002/30064* (2013.01); *A61F 2002/3084* (2013.01); *A61F 2002/3093* (2013.01); *A61F 2002/30266* (2013.01); *A61F 2002/30383* (2013.01); *A61F 2002/30433* (2013.01); *A61F 2002/30495* (2013.01); *A61F 2002/30525* (2013.01); *A61F 2002/30538* (2013.01); *A61F 2002/30556* (2013.01); *A61F 2002/30593* (2013.01); *A61F 2002/30601* (2013.01); *A61F 2002/30624* (2013.01); *A61F 2002/30632* (2013.01); *A61F 2002/30828* (2013.01); *A61F 2002/4628* (2013.01); *A61F 2002/4629* (2013.01)

(56) References Cited

U.S. PATENT DOCUMENTS

| | | | |
|---|---|---|---|
| 5,554,191 A * | 9/1996 | Lahille | A61B 17/1757 623/17.11 |
| 5,653,763 A | 8/1997 | Errico | |
| 5,658,335 A | 8/1997 | Allen | |
| 6,176,882 B1 | 1/2001 | Biedermann et al. | |
| 6,190,414 B1 | 2/2001 | Young | |
| 6,685,742 B1 | 2/2004 | Jackson | |
| 6,723,126 B1 | 4/2004 | Berry | |
| 6,953,477 B2 | 10/2005 | Berry | |
| 6,962,606 B2 | 11/2005 | Michelson | |
| 7,655,046 B2 * | 2/2010 | Dryer | A61F 2/4611 623/17.15 |
| 7,708,779 B2 | 5/2010 | Ede | |
| 8,011,551 B2 | 9/2011 | Marczyk | |
| 8,070,813 B2 | 12/2011 | Grotz et al. | |
| 8,075,600 B2 | 12/2011 | Schlapfer | |
| 8,303,663 B2 | 11/2012 | Jimenez et al. | |
| 8,491,657 B2 * | 7/2013 | Attia | A61F 2/447 623/17.16 |
| 8,685,095 B2 * | 4/2014 | Miller | A61F 2/447 623/17.11 |
| 9,271,777 B2 | 3/2016 | Nichols et al. | |
| 2002/0173817 A1 | 11/2002 | Kletschka et al. | |
| 2006/0069436 A1 | 3/2006 | Sutton | |
| 2006/0224241 A1 | 10/2006 | Butler et al. | |
| 2007/0198089 A1 | 8/2007 | Moskowitz et al. | |
| 2008/0091211 A1 * | 4/2008 | Gately | A61F 2/4611 606/99 |
| 2009/0118765 A1 | 5/2009 | Mueller et al. | |
| 2009/0299478 A1 | 12/2009 | Carls et al. | |
| 2010/0168861 A1 | 7/2010 | Yundt | |
| 2010/0274299 A1 | 10/2010 | Lawson et al. | |
| 2011/0106172 A1 | 5/2011 | Wallenstein et al. | |
| 2011/0160861 A1 | 6/2011 | Jimenez et al. | |
| 2011/0172716 A1 | 7/2011 | Glerum | |
| 2011/0245927 A1 | 10/2011 | Farris | |
| 2012/0029636 A1 | 2/2012 | Ragab | |
| 2012/0271422 A1 * | 10/2012 | Miller | A61F 2/4611 623/17.16 |
| 2012/0310350 A1 | 12/2012 | Farris et al. | |
| 2014/0288652 A1 | 9/2014 | Boehm | |
| 2015/0025634 A1 | 1/2015 | Boehm | |
| 2015/0094814 A1 | 4/2015 | Emerick | |
| 2015/0351925 A1 | 12/2015 | Emerick | |
| 2016/0151172 A1 | 6/2016 | Nichols | |

FOREIGN PATENT DOCUMENTS

| | | |
|---|---|---|
| WO | 2010033445 | 3/2010 |
| WO | 2010120782 | 10/2010 |
| WO | 2011011609 | 1/2011 |
| WO | 2013155418 | 10/2013 |
| WO | 2013158294 | 10/2013 |
| WO | 2014116891 | 7/2014 |

OTHER PUBLICATIONS

International Preliminary Report on Patentability issued for PCT Application PCT/US2014/037884 dated Nov. 17, 2015.
Written Opinion of the International Searching Authority issued for PCT Application PCT/US2014/037884 dated Dec. 10, 2014.

* cited by examiner

ADJUSTABLE INTERBODY FUSION DEVICES AND METHODS OF USE

CROSS-REFERENCE TO RELATED APPLICATION

This application is a continuation of U.S. Non-Provisional patent application Ser. No. 15/991,460 filed on May 29, 2018, now U.S. Pat. No. 10,278,832, which is a continuation of U.S. Non-Provisional patent application Ser. No. 14/890,837 filed on Nov. 12, 2015, now U.S. Pat. No. 9,980,825, which was a 371 National Phase application of PCT/US2014/037884 filed on May 13, 2014, which claimed priority benefit under 35 U.S.C. § 119(e) to U.S. provisional application No. 61/822,620 filed May 13, 2013, each of which is hereby incorporated herein by reference in its entirety.

TECHNICAL FIELD

The present invention relates generally to general surgery, orthopedic and neurosurgical implants used for insertion within a space between hard tissue structures, and more specifically, but not exclusively, concerns devices implanted between bones to replace resected, fractured or diseased structures and to maintain or reestablish proper spacing between two bones.

BACKGROUND OF THE INVENTION

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY OF THE INVENTION

Advancement of the state of interbody fusion devices and implants and the surgical management relating to the clinical presentation of damaged tissue structures within the body is believed desirable. Example embodiments of the invention that satisfies the need for improvements to an expandable interbody fusion device used to treat patients suffering from either diseased or damaged disc or other tissue structures includes a superior member coupled to a body member.

The present invention provides in one aspect, an interbody fusion device including a base member, a top member, and at least one movement mechanism. The base member includes at least one pivot cylinder and at least one hinge channel. The top member includes at least one pivot cylinder and at least one hinge channel. The at least one pivot cylinder of the base member engages the at least one hinge channel of the top member and the at least one pivot cylinder of the top member engages the at least one hinge channel of the base member. The at least one movement mechanism engages the top member and the body member.

The present invention provides in another aspect, an interbody spacer system including an insertion tool and an interbody fusion device. The insertion tool may include a handle, an insertion end, at least one tube extending distally away from the handle and connecting the handle and the insertion end. The tool may also include a securement mechanism and at least one adjustment mechanism coupled to the handle and extending through the at least one tube and protruding from the insertion end. The tool may further include a first knob for actuating the securement mechanism and at least one second knob for actuating the adjustment mechanism. The interbody fusion device may include an inferior member, a superior member, and at least one movement mechanism engaging the superior member and the inferior member. The inferior member includes at least one of a pivot cylinder and a hinge channel, a tool alignment opening for receiving the securement mechanism of the insertion tool, and an adjustment opening adjacent the tool alignment opening for receiving the at least one adjustment mechanism. The superior member includes at least one pivot cylinder and a hinge channel. The at least one pivot cylinder of the inferior member engages the at least one hinge channel of the superior member and the at least one pivot cylinder of the superior member engages the at least one hinge channel of the inferior member.

The present invention provides in yet another aspect, a base member, a top member, and at least one movement mechanism. The base member includes at least one pivot cylinder. The top member includes at least one hinge channel, at least one contact area on a bottom surface of the top member, and at least one stop pin extending out from the at least one contact area. The at least one pivot cylinder engages the at least one hinge channel to allow pivoting motion. The at least one movement mechanism engages the at least one contact area of the top member and the base member to facilitate movement therebetween.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

DETAILED DESCRIPTION FOR CARRYING OUT THE INVENTION

Generally stated, disclosed herein is an interbody fusion device or interbody device that typically includes a top member, a base member, and at least one expansion mechanism. Further, the interbody fusion device may include an extendable/retractable member or expansion assembly and an expansion tool for expansion and contraction of the interbody device. The retractable member extending in a vertical direction. As used herein, the terms "interbody fusion device," "medical device," "device," "interbody device" and "implant" may be used interchangeably as they essentially describe the same type of device. Further, the corresponding expansion tool may also be referred to as "tool" or "instrument" and these terms may be used interchangeably. Finally, described herein is a surgical method for using the interbody fusion device to maintain a space between two vertebral bodies within a patient suffering from a diseased or damaged disc or spinal column.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 1:
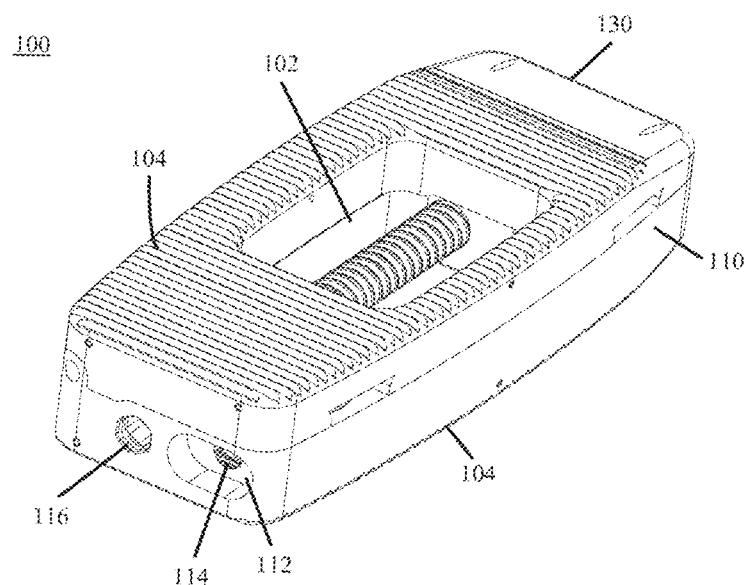
FIG. 1 is a posterior perspective view of one embodiment of an expandable interbody fusion device, in accordance with an aspect of the present invention.
Figure 2:
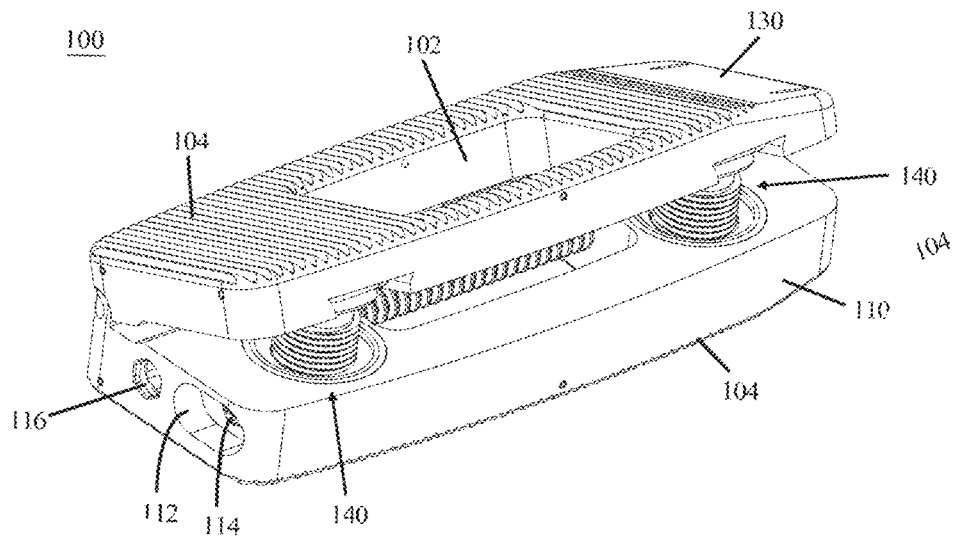
FIG. 2 is a posterior perspective view of the expandable interbody fusion device of FIG. 1 with the moveable members extended, in accordance with an aspect of the present invention.
Figure 3:
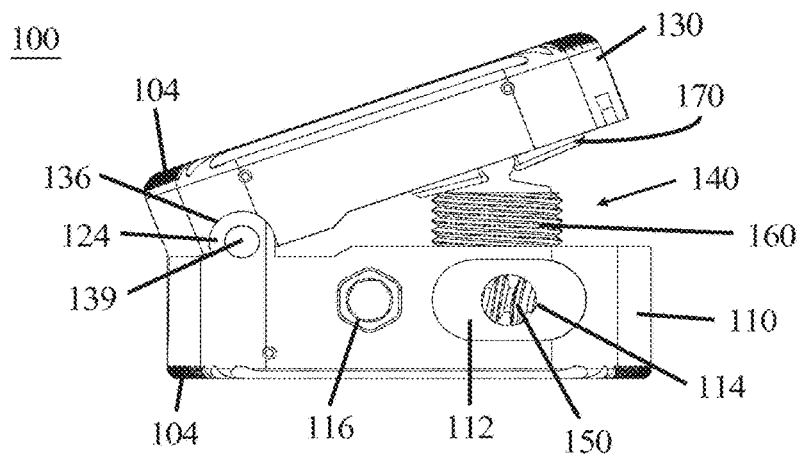
FIG. 3 is a posterior view of the expandable interbody fusion device of FIG. 1 with the moveable members extended, in accordance with an aspect of the present invention.

As depicted in FIGS. 1-3, the general arrangement of an adjustable interbody fusion device 100, in one embodiment, includes a base member 110, at least one moveable top member 130, and an expansion mechanism 140. The top member 130 may be detachably coupled to the body member 110. As used herein, the terms "base member," "body member," "bottom member" and "inferior member" may be used interchangeably herein as they essentially describe the same element of the device. Also as used herein, the terms "top member," "superior member," and "moveable member" may be used interchangeably as they essentially describe the same element of the device. The device 100 as seen in FIG. 1 may have, for example, a generally rectangular geometry with various configured long sides to facilitate insertion and bone coverage. Although it would be understood by one skilled in the art that other outside configurations can be used.

As seen in FIGS. 1 and 2, base member 110 may have at least one through hole or central opening 102 for insertion of bone graft material disposed on the inferior and superior bone contacting surfaces 104. The opening 102 typically extends through both bone contacting surfaces 104 of the base and top members 110, 130 and into the inner cavity of the assembled device 100. The size and configuration of the opening 102 allow the surgeon to place bone graft material inside the implant 100 to achieve a continuous fusion between the inferior and superior vertebral bodies.

As shown in FIG. 1, the superior and inferior bone contacting surfaces 104 may be generally parallel to each other. However, the expansion mechanism or movement mechanism 140 (these names may be used interchangeably) will allow the user to angle or raise one side of the bone contacting surface 104 of the top member 130 relative to the bone contacting surface 104 of the base member 110 as seen in FIGS. 2 and 3, wherein the near side is fully expanded and the far side remains stationary. FIGS. 1-4 show the bone contacting surfaces 104 to have teeth-like or tine structures projecting away from the superior and inferior surfaces. One skilled in the art would recognize that other surface treatments may be applied to the bone contacting surfaces 104 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial or ingrowth surfaces, and ridge structures. It is also understood that the bone contacting surfaces 104 may be coated with nano-surfacing, bioactive or bone/tissue ingrowth coatings.

Figure 4:
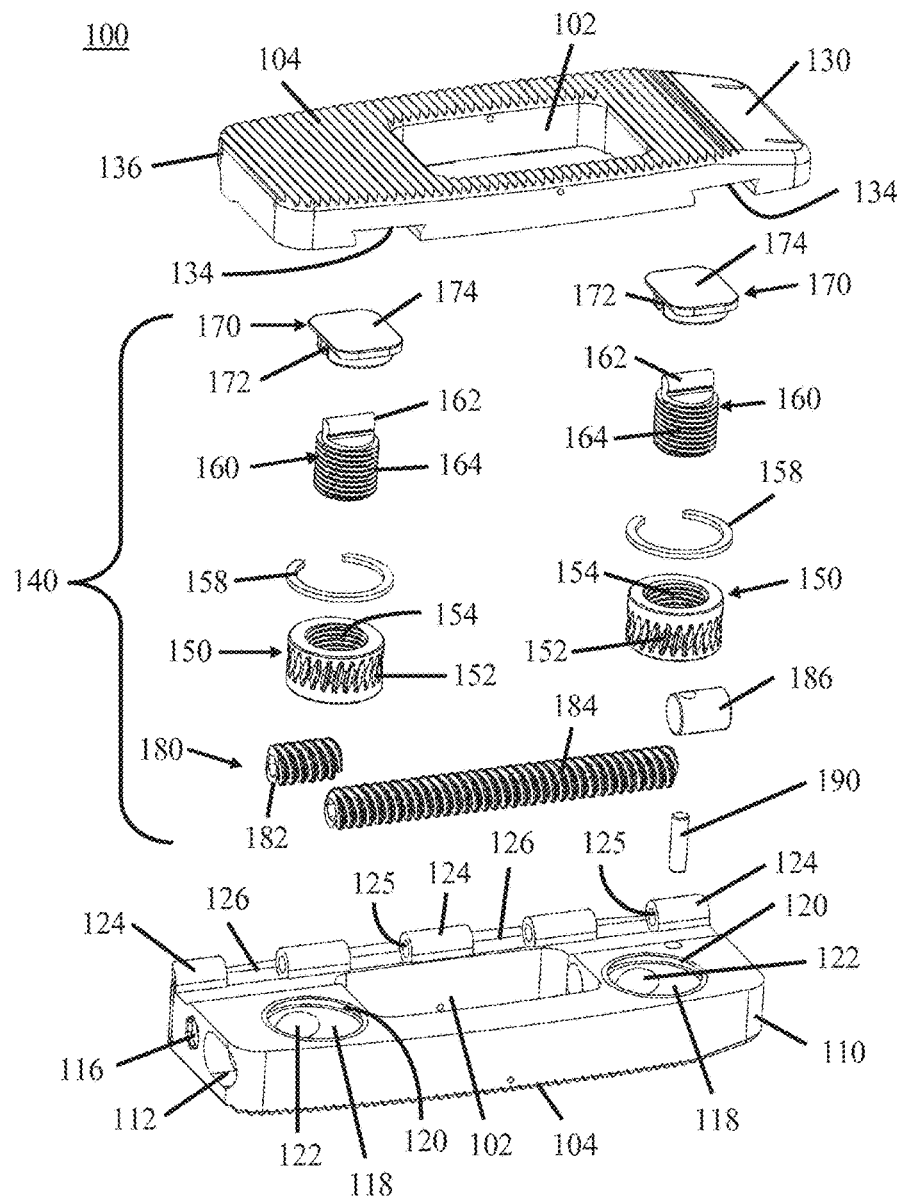
FIG. 4 is an exploded view of the expandable interbody fusion device of FIG. 1, in accordance with an aspect of the present invention.
Figure 5:
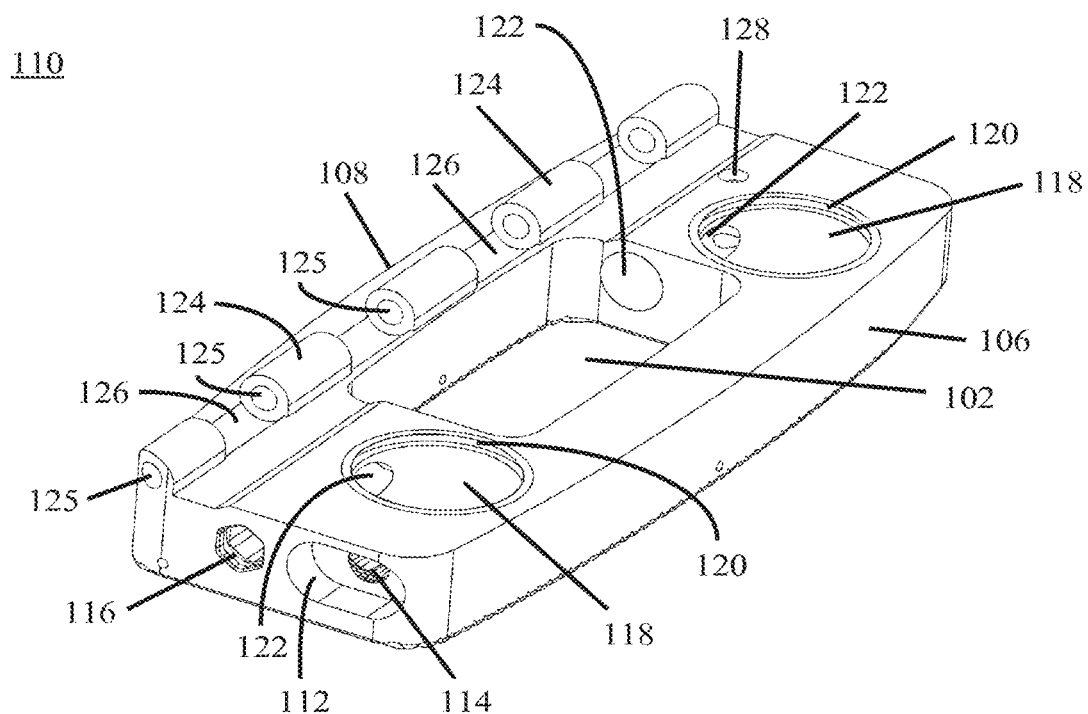
FIG. 5 is a superior perspective view of the expandable interbody fusion device of FIG. 1, showing only the base or bottom member, in accordance with an aspect of the present invention.

As seen in FIGS. 4 and 5, the base member 110 may also include a tool alignment opening 112 on the posterior end of the base member 110, a tool attachment opening 114 in the tool alignment opening 112, and an adjustment opening 116 on the posterior end of the base member 110 and which may be adjacent to the tool alignment opening 112, as seen in FIGS. 1-5. The base member 110 may also include at least one hole or lumen 118 near the proximal and/or distal ends of the base member 110 to house an expansion mechanism 140, which will be discussed in greater detail below. In one embodiment, as illustrated in FIGS. 1-11, the base member 110 may include, for example, two holes 118, although only one hole 118 as well as more than two holes 118 are also contemplated. The holes 118 may have a smooth vertical wall to facilitate insertion and unrestricted rotation of a cylindrical gear 150 of the expansion mechanism 140. The holes 118 of the base member 110 may also include an internal circumferential shoulder 120 and a channel 122 extending from the adjustment opening 116 interiorly along a lateral side of the base member 110 to engage the holes 118. The base member 110 may also include at least one pivot cylinder 124, at least one hinge channel 126, and an opening 128. The at least one pivot cylinder 124 and the at least one hinge channel 126 may alternate as depicted in FIGS. 4 and 5.

Figure 6:
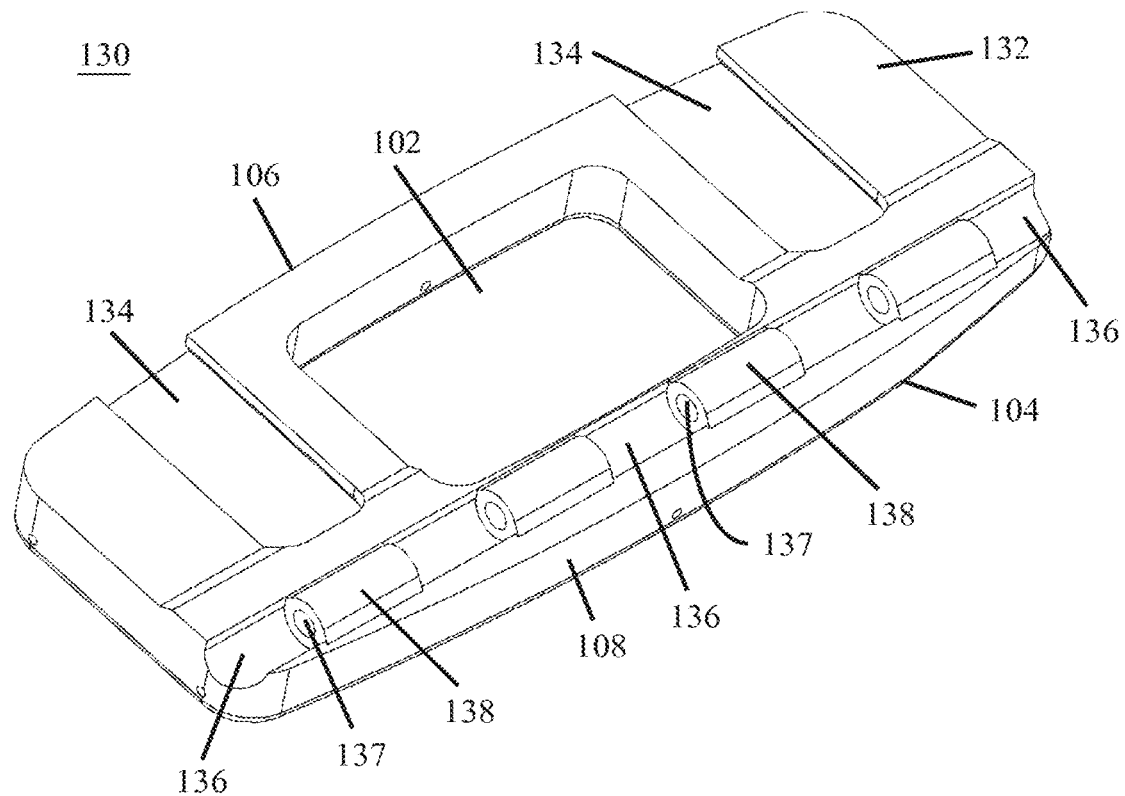
FIG. 6 is an inferior perspective view of the expandable interbody fusion device of FIG. 1, showing only the top or superior member, in accordance with an aspect of the present invention.

As seen in FIGS. 4 and 6, the top or superior member 130 also includes an undersurface 132 with at least one relief area 134 that is adjacent to the central opening 102. The central opening 102 may be configured to permit the insertion of bone graft material into the inner cavity of the implant 100 prior to or after implantation. In one embodiment, as illustrated in FIGS. 1-11, the top member 130 may include, for example, two relief areas 134, although a single relief area 134 as well as more than two relief areas 134 are also contemplated. The at least one relief area 134 may extend from a position on the undersurface 132 of the top member 130 to at least one lateral side of the top member 130. The relief areas 134 may be substantially planar and may be aligned with the holes 118 in the base member 110. The relief areas 134 are relatively rectangular with the long axis of the rectangle extending along the lateral axis of the top member 130 or perpendicular to the longitudinal axis of the device 100.

As seen in FIGS. 4-6, the relief areas 134 may be configured to mate with at least one correspondingly shaped load head 170 of the an expansion mechanism 140. The top member 130 may also include at least one hinge channel 136 and at least one pivot cylinder 138 and the hinge channels 136 may alternate with the pivot cylinders 138, as depicted in FIG. 6. The at least one hinge channel 136 of the top member 130 may mate with the at least one pivot cylinder 124 of the base member 110 and the at least one pivot cylinder 138 of the top member 130 may mate with the at least one hinge channel 126 of the base member 110 to enable the implant 100 to extend on a first lateral side 106 while remaining closed on a second lateral side 108. A pin 139 may be inserted into openings 125, 137 in the pivot cylinders 124, 138, respectively, to pivotally secure the top member 130 to the base member 110. The pivot cylinders 124 and hinge channels 126 of the base member 110 and the hinge channels 136 and pivot cylinders 138 of the top member 130 allow the hinge channels 126, 136 to pivot or rotate around the outer diameter of the pivot cylinders 124, 138 when the at least one expansion assembly 142 is extended or retracted causing the top member 130 to tilt or slant relative to the base member 130. In another embodiment, the base member 110 may include a pivot cylinder 124 and the top member 130 may include a hinge channel 136, alternatively, the base member 110 may include a hinge channel 126 and the top member 130 may include a pivot cylinder 138.

Figure 7:
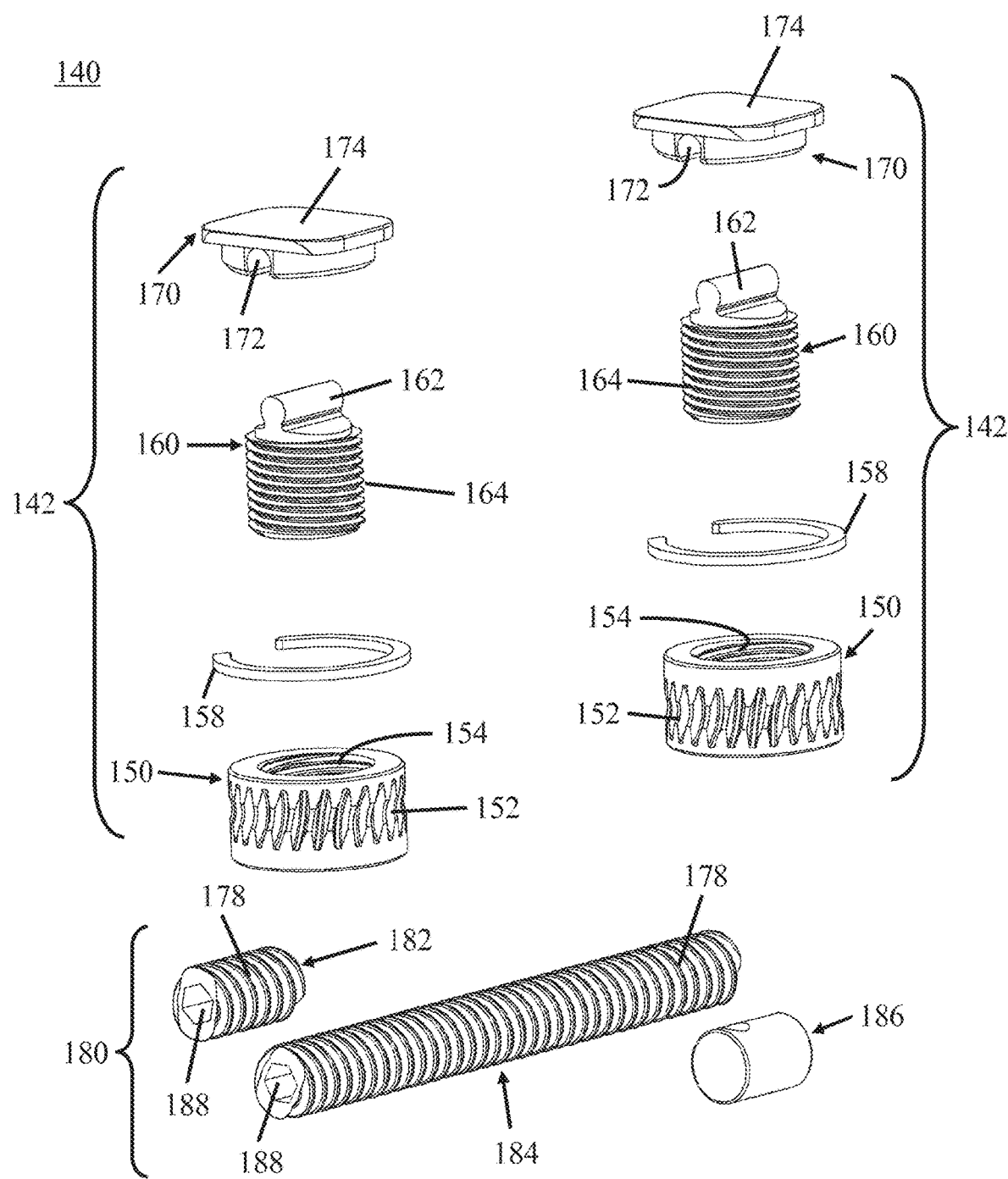
FIG. 7 is an exploded view of the expansion mechanism of the expandable interbody fusion device of FIG. 1, in accordance with an aspect of the present invention.

Referring now to FIG. 4 with continued reference to FIGS. 5 and 6, an exploded view of all of the components that comprise the implant 100 is shown. As shown in FIG. 7, the expansion mechanism 140 of the implant 100 includes at least one expansion assembly 142 and a drive rod 180. In one embodiment, as shown in FIG. 7, the expansion mechanism 140 includes two expansion assemblies 142. The expansion assemblies 142 may include a cylindrical gear 150, a support means 158, a threaded rod 160, and a load head 170. The vertical cylinder or cylindrical gears 150 (these names may be used interchangeably) may nest or be suspended within the holes 118 of the base member 110. The cylindrical gears 150 may include external substantially vertical depressions or circumferential serial depressions 152 positioned on the outer surface of the gears 150 which extend around the entire circumference. For example purposes, the gears 150 may have a smooth surface, above and below the substantially vertical depressions 152. Positioning the circumferential serial depressions 152 around the central portion of the gears 150 may maximize strength and improve trackability when the cylindrical gears 150 engage the drive rod 180. The circumferential serial depressions 152 may also include uniquely oriented thread patterns. In addition, the gears 150 may include internal threads 154 on the interior surface of the gears 150.

Figure 8:
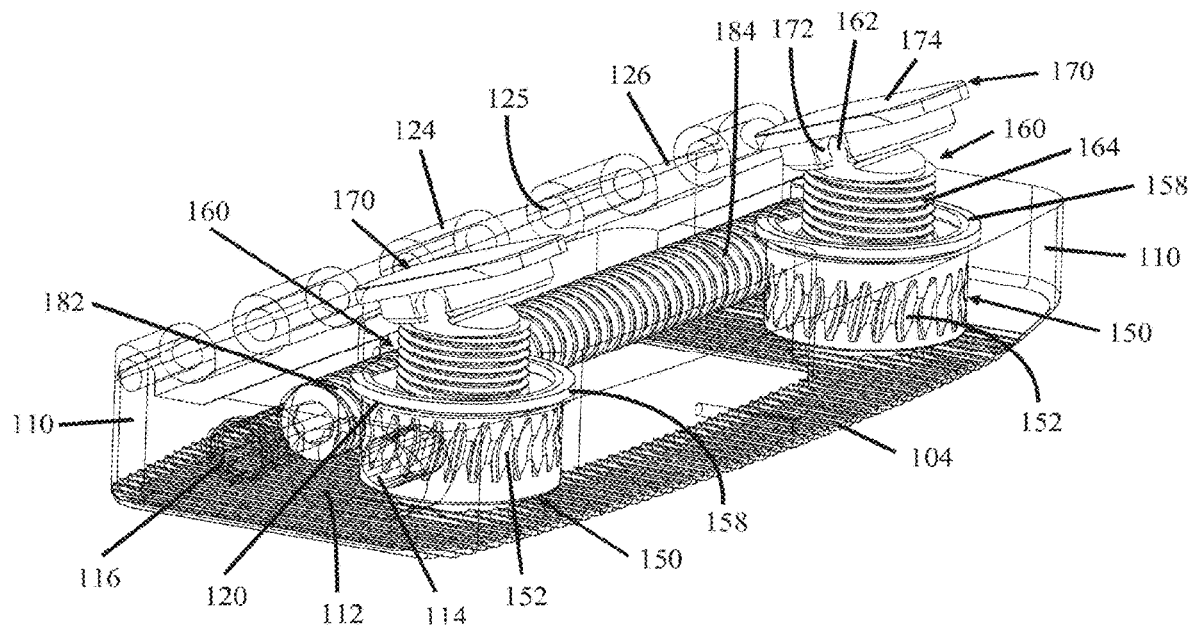
FIG. 8 is a posterior elevational view of the expandable interbody fusion device of FIG. 1 without the top member, showing the expansion assemblies seated in the transparent base member, extended and tilted to accommodate the slanted top member, in accordance with an aspect of the present invention.

As shown in FIG. 8, the support means 158 may sit on the shoulders 120 of the base member 110 and function to maintain the expansion assemblies 142 in a vertical orientation relative to the base member 110 and aligned with the holes 118. The support means 158 may also be used adjacent to the gears 150 and threaded rods 160 and may hold the gears 150 in the holes 118. The support means may, for example, be in the form of a ring, snap ring, washer or other similar type of structure that will secure the expansion assemblies 142 to the base member 110. The shoulders 120 may also operate as bearing surfaces against which the support means 158 contacts to facilitate the rotation of the expansion assemblies 142 when actuated.

As shown in FIGS. 4, 7 and 8, the threaded rods 160 may include a pivot cylinder 162 located on the top or superior end of the threaded rods 160. The terms "pivot cylinder," "arcuate surface" and "curved surface" may be used interchangeably herein as they all refer to the same structure of the threaded rods. The threaded rods 160 may also include external threads 164 extending along its length. The external threads 164 may be configured to match the internal threads 154 of the gears 150. The pivot cylinder 162 of the threaded rods 160 may be inserted into a distal channel 172 of the load heads 170. These constructs allow the load heads 170 to pivot, slide, or rotate around the outer diameter of the pivot cylinders 162 when the threaded rods 160 are extended causing the top member 130 to tilt or slant. Tilted or slanted load heads 170 are shown in FIGS. 3 and 8. The load heads 170 may also include superior head surfaces 174. The superior head surfaces 174 may be shaped to match with the corresponding relief areas 134 on the undersurface 132 of the top member 130. The superior head surfaces 174 are configured to slide within the reliefs 134 of the undersurface 132, if necessary, to allow for the expansion assemblies 142 to lengthen to create the angled relationship of the top member 130 relative to the base member 110. The reliefs 134 in the undersurface 132 and the correspondingly shaped load heads 170 facilitate the angulation process and the load transfer between the top member 130 and the base member 110 while avoiding potential binding of the expansion assemblies 142 during the expansion and retraction process.

The drive rod 180 of the expansion mechanism 140 may be inserted into the adjustment opening 116 and sit in the channel 122 of the base member 110, as shown in FIGS. 4, 7, and 8. The drive rod 180 may include of a first worm gear 182, a second worm gear 184 and a cylindrical shaft 186. The first worm gear 182 and the second worm gear 184 may also have tool openings 188 at a second end opposite the first end with the cylindrical shaft 186 for coupling with a tool 200. The tool opening 188 of the second worm gear 184 may mate with a corresponding protrusion on the first end of the first worm gears 182 to facilitate simultaneous rotation of both worm gears 182, 184. In another embodiment, the drive rod 180 may include a single worm gear and a cylindrical shaft 186, the single worm gear would have a length to enable engagement with both gears 150 simultaneously. In addition, the cylindrical shaft 186 may include an opening 176 for mating with a pin 190 to secure the drive rod 180 in the base member 110 to enable adjustment of the top member 130 without the drive rod 180 moving out of the implant 100. The pin 190 may also prevent the drive rod 180 from advancing out of the implant 100 after implantation into the patient's spine. By off-centering the adjustment opening 116 and the channel 122 from the longitudinal axis of the device 100, the worm gears 182, 184 of the drive rod 180, which are inserted into the channel 122, intersect with the holes 118 of the base member 110. The worm gears 182, 184 may be configured to engage with the gears 150 of the expansion assemblies 142 which sit in the holes 118 of the base member 110. FIG. 8 shows the assembled implant 100 without the top member 130 with the drive rod 180 positioned and extending through the length of the base member 110.

Figure 12:
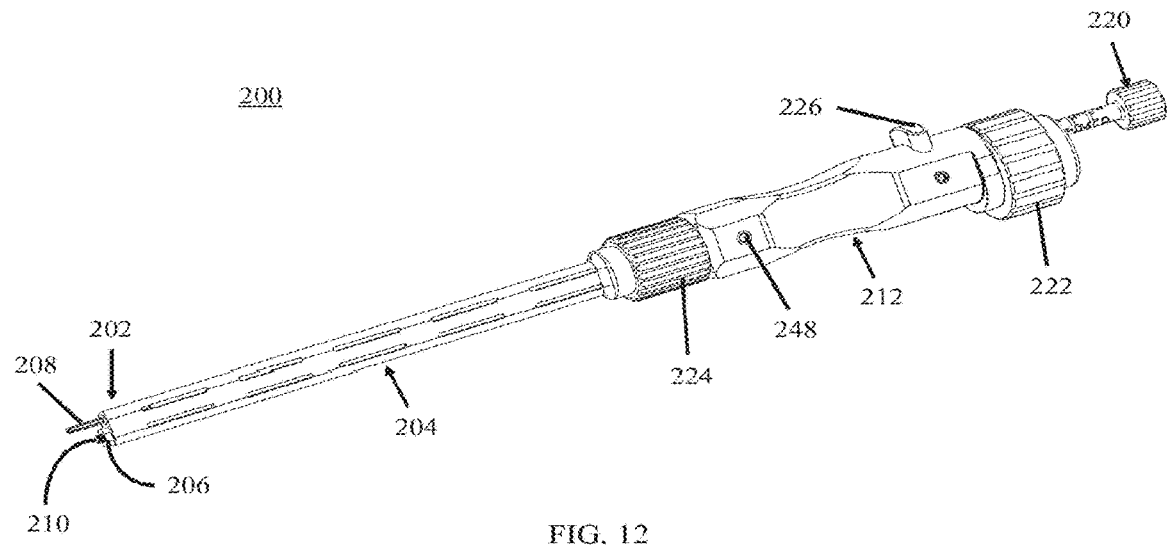
FIG. 12 is a top perspective view of an expansion tool, in accordance with an aspect of the present invention.
Figure 13:
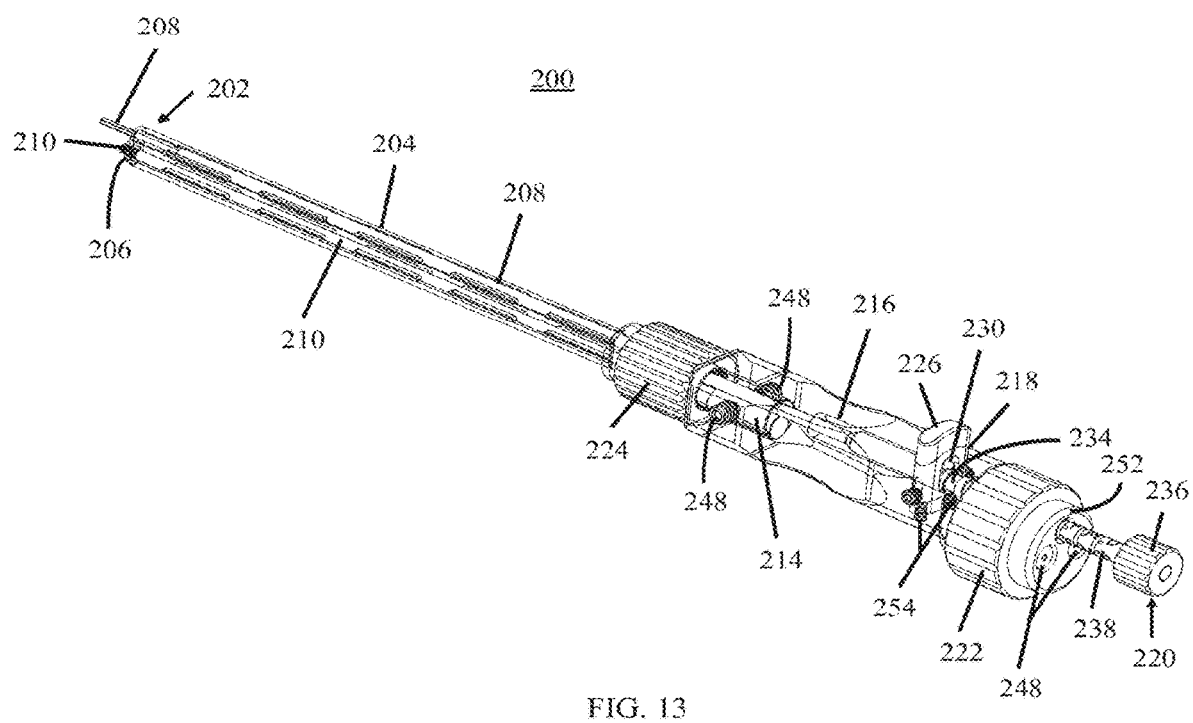
FIG. 13 is a top perspective view of the expansion tool of FIG. 12 with a transparent handle portion and housing portion, in accordance with an aspect of the present invention.
Figure 14:
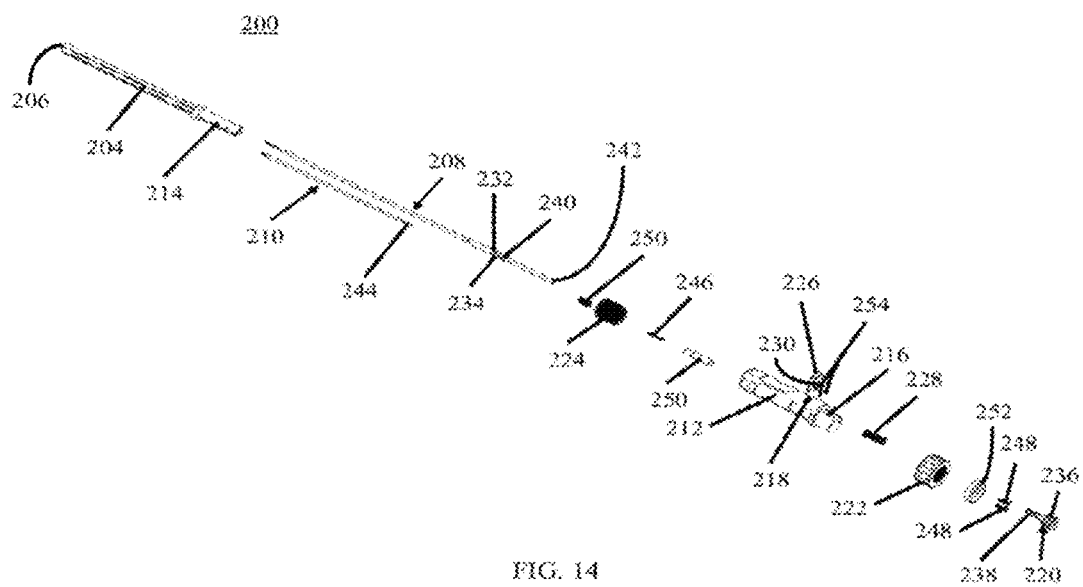
FIG. 14 is an exploded view of the expansion tool of FIG. 12, in accordance with an aspect of the present invention.

When the implant 100 is inserted into a patient using tool 200, as shown in FIGS. 12-14, the tool 200 engages the alignment opening 112, the attachment opening 114 and the adjustment opening 116, as described in greater detail below. Once the tool 200 is inserted into the patient between two vertebrae, the drive rod 180 with the gears 150 function to mirror the rotational movement exerted by the tool 200, described in greater detail below, and translate the movement to the gears 150. The expansion mechanism 140 functions to convert rotation movement of the gears 150 into linear or translational movement of the load heads 170 positioned at the superior end of the threaded rods 160. Rotation of the gears 150 will result in a travel distance of the threaded rods 160 when the expansion mechanism 140 is actuated by the tool 200. As the gears 150 are coupled to the drive rod 180, the coupled gears 150 will turn as the drive rod 180 is rotated, thus avoiding the need for the tool 200 to pass through the entire length of the channel 122 to engage the gear 150 on the far end of the implant 100. Specifically, the second worm gear 184 is coupled to the drive rod 180 on the far end of the implant 100 and the first worm gear 182 is coupled to the drive rod 180 on the near end of the implant 100.

With continued reference to FIGS. 1-11, as the drive rod 180 is rotated by the tool 200 the teeth 178 of the worm gears 182, 184 of the drive rod 180 are configured to mate with the substantially vertical depressions 152 of the gears 150. As described above, the expansion assemblies 142 act to covert rotational movement of the gears 150 into translational movement of the threaded rods 160. This is achieved by allowing free rotational movement of the gears 150 while restricting the rotation of the threaded rods 160. By restricting the rotation of the threaded rods 160, the rods translate in either an upward or downward direction relative to the gears 150 depending upon whether the threads (external and internal) 154, 164 are oriented in a right-handed or left-handed direction. As discussed above, when the threaded rods 160 move, the load heads 170 contact the relief areas 134 of the undersurface 130 of the top member 130 to either move it away from or towards the base member 110. In other words, the height of the implant 100 either increases or decreases or the bone contacting surface 104 will be angled relative to the base member 110 depending on the rotational direction of the tool 200.

Figure 9:
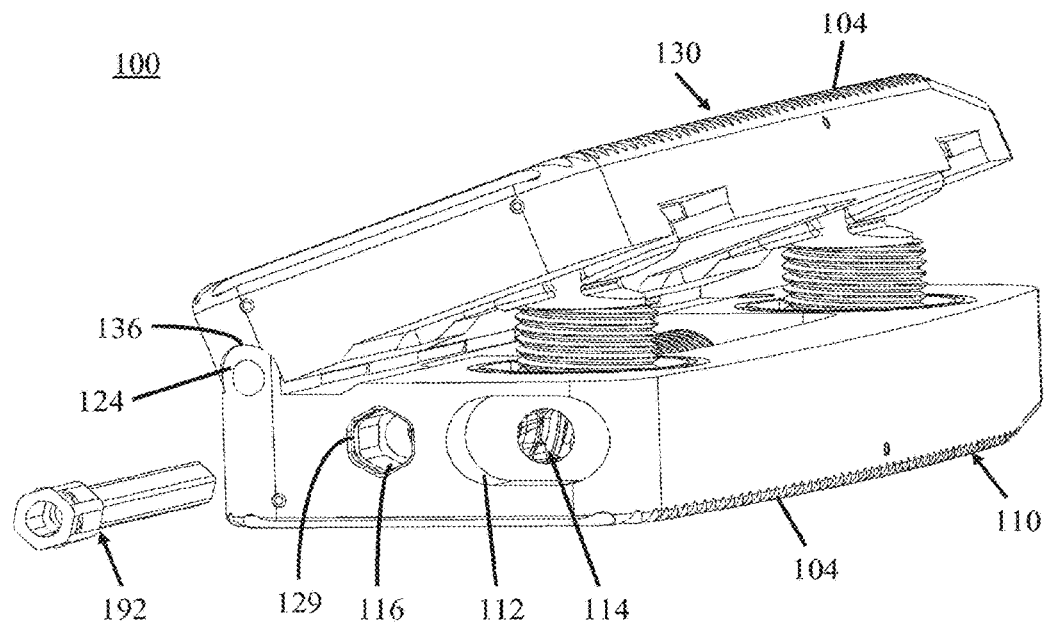
FIG. 9 is a partially exploded posterior perspective view of the expandable interbody fusion device of FIG. 1 showing the locking mechanism being inserted into the interbody fusion device, in accordance with an aspect of the present invention.
Figure 10:
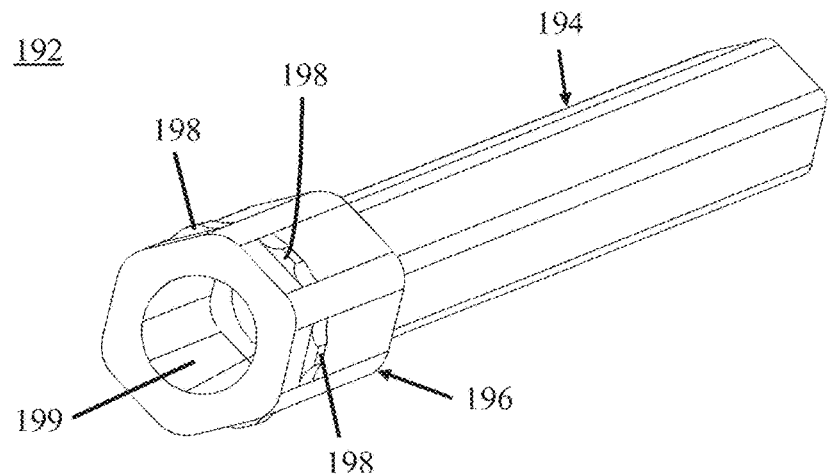
FIG. 10 is an isometric view of the locking mechanism of FIG. 9, in accordance with an aspect of the present invention.
Figure 11:
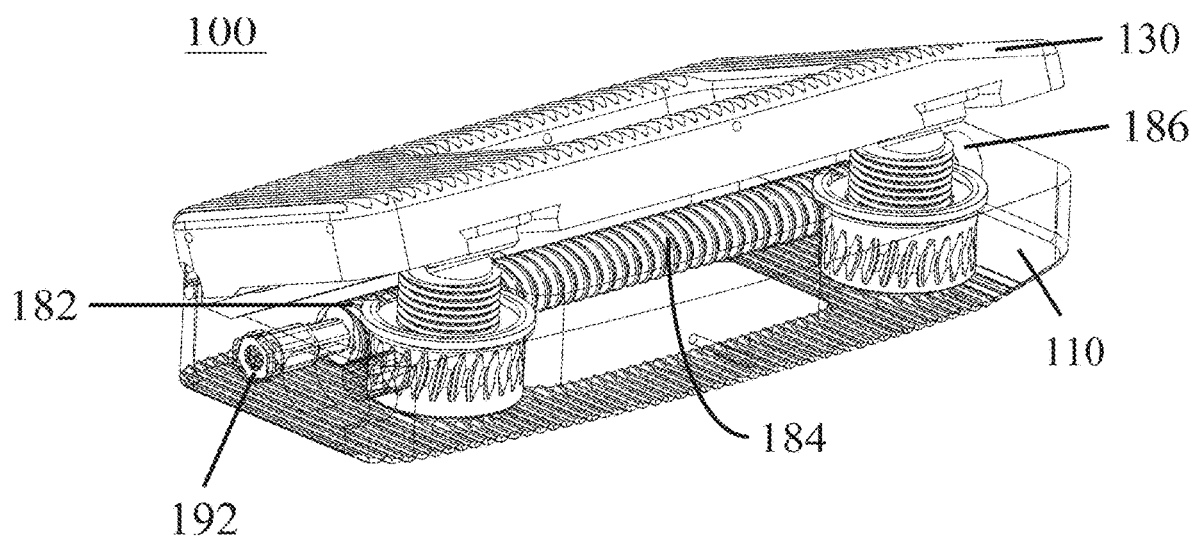
FIG. 11 is a posterior perspective view of the expandable interbody fusion device of FIG. 1 with a transparent base member showing a drive rod and locking mechanism, in accordance with an aspect of the present invention.

Referring now to FIGS. 9-11, a locking mechanism 192 for an embodiment of the adjustable interbody fusion device 100 is shown. As shown in FIG. 10, the locking mechanism 192 may include a shaft 194 extending out from a head 196. The head 196 may include a plurality of protrusions 198 for engaging the lip 129 in the adjustment opening 116 of the base member 110 to secure the locking mechanism 192 in the base member 110. The head 196 may also include an opening 199 for engaging the insertion tool 200 or a similar tool. The shaft 194 of the locking mechanism 192 may have a shape which corresponds to the shape of the tool openings 188 in the worm gears 182, 184 of the drive rod 180, for example, the shape may be a hexagon, square, or other multi-lobed configuration allowing the shaft 194 of the locking mechanism 192 to fit securely within the openings 186 of the drive rod 180. The shaft 194 of the locking mechanism 192 may be inserted, for example, through the opening 186 of the first worm gear 182 and into the opening 186 in the second worm gear 184. Alternatively, the shaft 194 of the locking mechanism 192 may be inserted, for example, into the opening 186 of the first worm gear 182 to lock both the first and second worm gears 182, 184 in the selected position where the first worm gear 182 includes a protrusion on the first end that engages the opening 186 in the second worm gear 184. Similarly, the head 196 may have a shape which corresponds to the shape of the adjustment opening 116, for example, the shape may be a circle, hexagon, square, or other multi-lobed configuration allowing the locking mechanism 192 to securely fit within the adjustment opening 116 of the base member 110 to secure the locking mechanism 192 in the implant 100 to maintain a desired expansion or retraction. Other shapes for the shaft 194 and the head 196 of the locking mechanism 192 are also contemplated. The locking mechanism 192 may be, for example, made of a rigid material or a deformable material. If the locking mechanism 192 is made of a deformable material it may be made slightly larger than the opening 186 in the drive rod 180 and/or the adjustment opening 116 in the base member 110, such that once it is inserted the larger size locks the drive rod 180 in the desired position.

Referring now to FIGS. 12-14, one embodiment expansion tool 200 designed to engage and insert the implant 100 into a patient is shown. The tool 200 is designed to engage the expansion mechanism 140. The insertion end 202 of the tool 200 may be configured with a housing 204 including a protrusion 206 shaped to correspond to the alignment opening 112 in the base member 110. The insertion end 202 may also include an adjustment mechanism 208 and a securement mechanism 210 which protrude out of the distal end of the housing 204. The adjustment mechanism 208 may be configured, for example, to have a hex male head, square, or other multi-lobed configuration that will allow for the user to rotate the knob 224 of the tool 200 and cause the expansion mechanism 140 to rotate. Opposite the insertion end 202, the tool 200 has a handle 212 which may be connected to the housing 204 by an attachment member 214. The attachment member 214 may be coupled to the housing 204 on the proximal end and secured to the handle 212 by fasteners 248, for example, screws, pins, rivets, and the like. The tube 214 may house the adjustment mechanism 208 and the securement mechanism 210 which may extend from the handle 212 to the insertion end 202 inside the housing 204.

As seen in FIG. 13, the handle 212 of the tool 200 may also include a first opening 216 along the longitudinal axis of the handle 212. In addition, the handle 212 of tool 200 may include a second opening 218 extending perpendicular to and engaging the first opening 216. The handle 212 may also include a first knob 220 which may be inserted into the first opening 216 at a proximal end of the handle 212 to engage the adjustment mechanism 208. An actuation bar 226 may be inserted into the second opening 218. A gear 228 may be inserted into the first opening 216 prior to inserting the first knob 220 enabling the gear 228 to engage the first knob 220 as it is inserted into the handle 212 to engage the adjustment mechanism 208. The knob 220 may include a head 236 with a shaft 238 extending out away from the inferior surface of the head 236. The shaft 238 of the knob 220 may also include an opening for mating with the adjustment mechanism 208 to secure the knob 220 to the adjustment mechanism 208.

A second knob 222 may couple to the proximal end of the handle 212 over the opening 216 and the gear 228. The gear 228 may include teeth on the exterior surface which engage corresponding grooves on the interior surface of the second knob 222. The second knob 222 may be rotatably secured to the handle 212 by an end plate 252 which may be attached to the handle 212 using fasteners 248, for example, screws. A third knob 224 may couple to the proximal end of the housing 204 at the distal end of the handle 212. The third knob 224 may also engage a gear 250 which aligns with a channel in the attachment means 214 of the housing 204. The gear 250 may include grooves circumferentially around the exterior surface that mate with corresponding grooves circumferentially around the interior surface of the third knob 224.

As seen in FIGS. 12 and 13, the adjustment mechanism 208 may pass into the first opening 216 from the proximal end of the handle 212. The adjustment mechanism 208 may be secured to the distal end of the shaft 238 of the knob 220 prior to insertion into the first opening 216 from the proximal end of the handle 212. A tool engagement end 242 of the adjustment mechanism 208 couples with the distal end of the shaft 238 to enable rotation of the adjustment mechanism 208. The tool engagement end 242 of the adjustment mechanism 208 when inserted into the first opening 216 passes through a hole 230 in the actuation bar 226 before engaging the shaft 238 of the knob 220. The adjustment mechanism 208 may include a first channel 232, a second channel 234, and a third channel 240 for engaging the hole 230 in the actuation bar 226 to secure the adjustment mechanism 208 at a desired length at the insertion end 202. The securement mechanism 210 may pass into the second opening 218 from the distal end of the handle 212 enabling engagement with the distal end of the shaft 238 of the knob 220 when inserted into the second opening 218 from the proximal end of the handle 212. In addition, the securement mechanism 210 may include a spring mechanism 246 inserted over the proximal end of the securement mechanism 210 to spring load the securement mechanism 210. The spring mechanism 246 may also engage an end member 250 in the handle 212 which may provide a bearing surface for the spring mechanism 246 to engage. A tool engagement end 244 of the securement mechanism 210 couples with a gear 250 which engages the interior surface of the third knob 224 to enable rotation of the securement mechanism 210. The tool engagement ends 242, 244 may have, for example, a hex male head, square, or other multi-lobed configuration to enable rotation of the adjustment mechanism 208 or securement mechanism 210, respectively.

During use, the tool 200 may be inserted into the implant 100 by aligning the protrusion 206 of the insertion end 202 of the tool 200 with the alignment opening 112 of the implant 100. The third knob 224 may then be rotated thereby rotating the gear 250 and the engaged securement mechanism 210. As the knob 224 is rotated the threaded end of the securement mechanism 210 engages the threads in the tool attachment opening 114 of the implant 100 to secure the implant 100 to the tool 200 for insertion into a patient. In addition, as the securement mechanism 210 engages the attachment opening 114 of the implant 100, the adjustment mechanism 208 of the tool will engage the opening 186 in the drive rod 180 of the implant 100.

Once the tool 200 and implant 100 are aligned and the shaft 238 of the knob 220 is coupled to the tool engagement end 242 of the adjustment mechanism 208, the adjustment mechanism 208 may be inserted into the first opening 216. As the adjustment mechanism 208 is inserted into the handle 212, the actuation bar 226 is depressed allowing for the adjustment mechanism 208 to pass through the hole 230 in the actuation bar 226. The adjustment mechanism 208 passes through the handle 212 and the housing 204 and extends out of the insertion end 202 to pass through the adjustment opening 116 of the implant 100 and engage the expansion mechanism 140. Once the adjustment mechanism 208 engages the expansion mechanism 140 the actuation bar 226 may be released to engage one of the channels 232, 234, 240 of the adjustment mechanism 208 and maintain the position of the adjustment mechanism 208 at a desired length.

After the actuation bar 226 of the handle 212 has engaged a channel 232, 234, 240, the implant 100 may then be inserted into the desired position in the patient. The head 236 of the knob 220 may then be rotated which in turn will rotate the distal end of the adjustment mechanism 208. As the head 236 of the knob 220 is rotated, the adjustment mechanism 208, which is coupled to the opening 186 in the drive rod 180, engages the expansion mechanism 140 and expands a side of the implant 100 to angle the top member 130 relative to the base member 110. The cogs or teeth 178 of the worm gears 182, 184 of the drive rod 180 are sized to mate with the corresponding serial depressions 152 of the gears 150 to facilitate rotation of the gears 150 when the knob 220 of the tool 200 is turned. Alternatively, the second knob 222 may be used to rotate the adjustment mechanism 208 to facilitate rotation of the gears 150 to expand a side of the implant 100. The first knob 220 enables slower rotation of the adjustment mechanism 208, while the second knob 222 enables faster rotation of the adjustment mechanism 208 enabling faster opening or closing of the implant 100. Once the desired expansion of the implant 100 is achieved, the tool 200 may then be removed from the patient.

In the embodiment shown in FIGS. 12-14, prior to removing the tool 200, the locking mechanism 192 may be inserted into the implant 100 to secure the top member 130 of the implant 100 in the desired expansion and/or retraction relative to the base member 110. The locking mechanism 192 may be inserted into the opening 186 in the drive rod 180 by removing the adjustment mechanism 208 and first knob 220 from the tool 200 by depressing the actuation bar 226 and pulling the knob 220 out of the opening 216. Once the adjustment mechanism 208 has been removed a locking tool, not shown, with a locking mechanism 192 coupled to an insertion end of the locking tool may be inserted into the opening 216 through the handle 212 and the housing 204 existing the insertion end 202 to engage the implant 100.

As the locking mechanism 192 is inserted into the base member 110 and the drive rod 180, the shaft 194 of the locking mechanism 192 fits securely within the opening 186 of the drive rod 180. In one embodiment, the shaft 194 may extend through the opening 186 in the first worm gear 182 and into the opening 186 in the second worm gear 184.

Alternatively, in another embodiment, a shorter shaft 194 may extend into the opening 186 in the first worm gear 182 and the first and second worm gears 182, 184 may be coupled such that the locking mechanism 192 inserted into the first worm gear 182 secures both the worm gears 182, 184 in the desired position. In addition, the plurality of protrusions 198 on the head 196 may engage the lip 129 in the adjustment opening 116 of the base member 110, as shown in FIGS. 9-11. The drive rod 180 may be recessed within the base member 110 to provide a cavity for insertion of the locking mechanism 192 into the base member 110, such that when the locking mechanism 192 is inserted into the base member 110 of the implant 100 it is flush with the exterior surface of the base member 110.

The tool 200 may be removed from the patient by removing the adjustment mechanism 208 or the locking insert mechanism. The adjustment mechanism 208 or the locking insert mechanism may be removed from the first opening 216 by depressing the actuation bar 226 to disengage the actuation bar 226 from the channel 232, 234, 240 or a channel in the locking insert mechanism, not shown. Once the actuation bar 226 is disengaged the adjustment mechanism 208 or the locking insert mechanism may be removed from the first opening 216. Next, the securement mechanism 210 may be disengaged from the implant 100 by rotating the third knob 224 which in turn rotates the securement mechanism 210. As the securement mechanism 210 rotates it disengages the threads 108 of the attachment opening 114 and the protrusion 206 of the insertion end 202 of the tool 200 slide out of the alignment opening 112. It is also contemplated that the above method for inserting the implant 100 using tool 200 may be performed in alternative orders.

Figure 15:
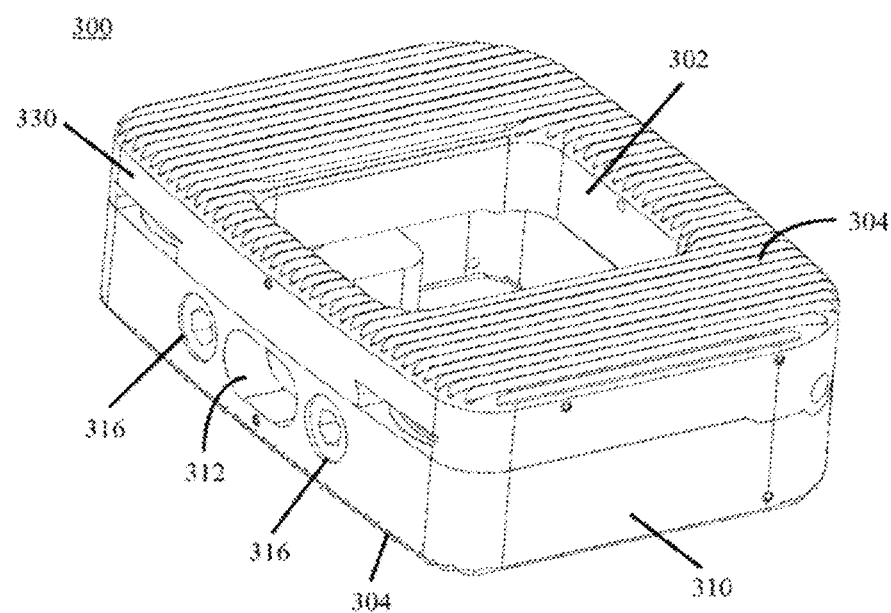
FIG. 15 is a perspective view of one embodiment of an expandable interbody fusion device, in accordance with an aspect of the present invention
Figure 16:
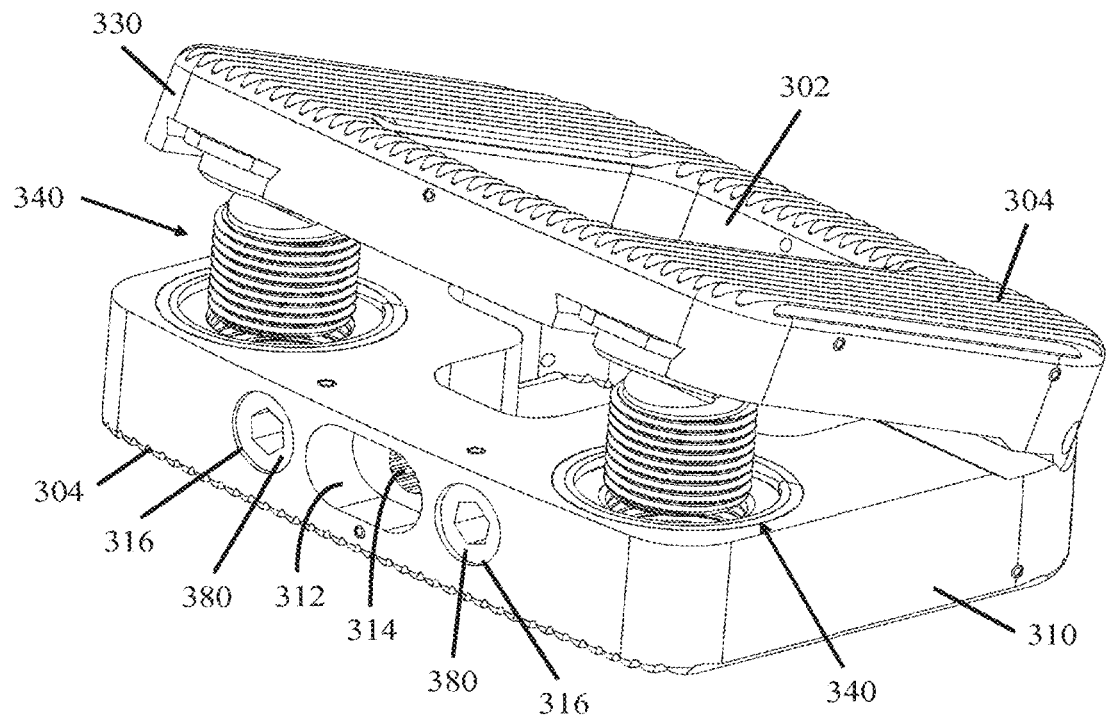
FIG. 16 is a perspective view of the expandable interbody fusion device of FIG. 15 with the moveable members extended, in accordance with an aspect of the present invention.
Figure 17:
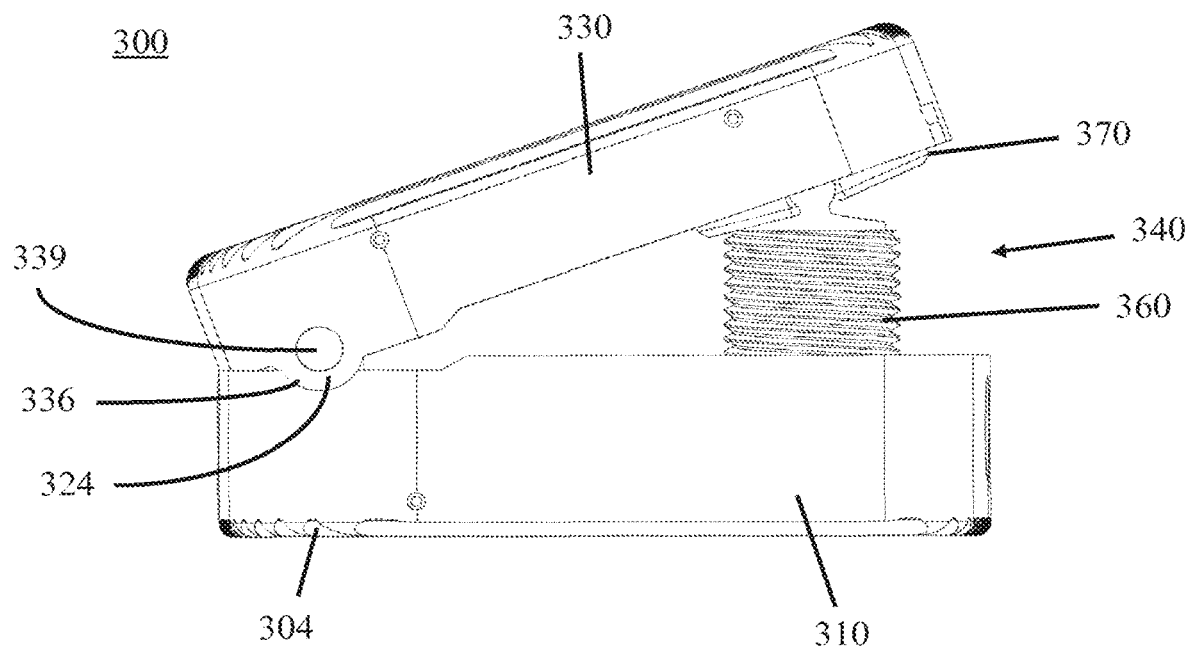
FIG. 17 is a posterior view of the expandable interbody fusion device of FIG. 15 with the moveable members extended, in accordance with an aspect of the present invention.

As depicted in FIGS. 15-17, the general arrangement of an adjustable interbody fusion device 300, in one embodiment, includes a base member 310, at least one moveable top member 330, and at least one expansion mechanism 340. The device 300 as seen in FIG. 15 may have, for example, a generally rectangular geometry with various configured long sides to facilitate insertion and bone coverage. Although it would be understood by one skilled in the art that other outside configurations, including square-like shapes, can be used. The top member 330 may be detachably coupled to the body member 310.

As seen in FIGS. 15 and 16, base member 310 may have at least one through hole or central opening 302 for insertion of bone graft material disposed on the inferior and superior bone contacting surfaces 304. The opening 302 typically extends through both bone contacting surfaces 304 of the base and top members 310, 330 and into the inner cavity of the assembled device 300. The size and configuration of the opening 302 allow bone graft material to be inserted inside the implant 300 to achieve a continuous fusion between the inferior and superior vertebral bodies.

As shown in FIG. 15, the superior and inferior bone contacting surfaces 304 may be generally parallel to each other. However, the expansion mechanisms or movement mechanisms 340 (these names may be used interchangeably) allow the user to angle one side of the bone contacting surface 304 of the top member 330 relative to the bone contacting surface 304 of the base member 310 as seen in FIGS. 16 and 17, wherein the near side is fully expanded and the far side remains retracted. As shown in FIGS. 15-18 the bone contacting surfaces 304 are of the type described above with reference to the bone contacting surfaces 104 of implant 100 and for brevity sake will not be described again here.

Figure 18:
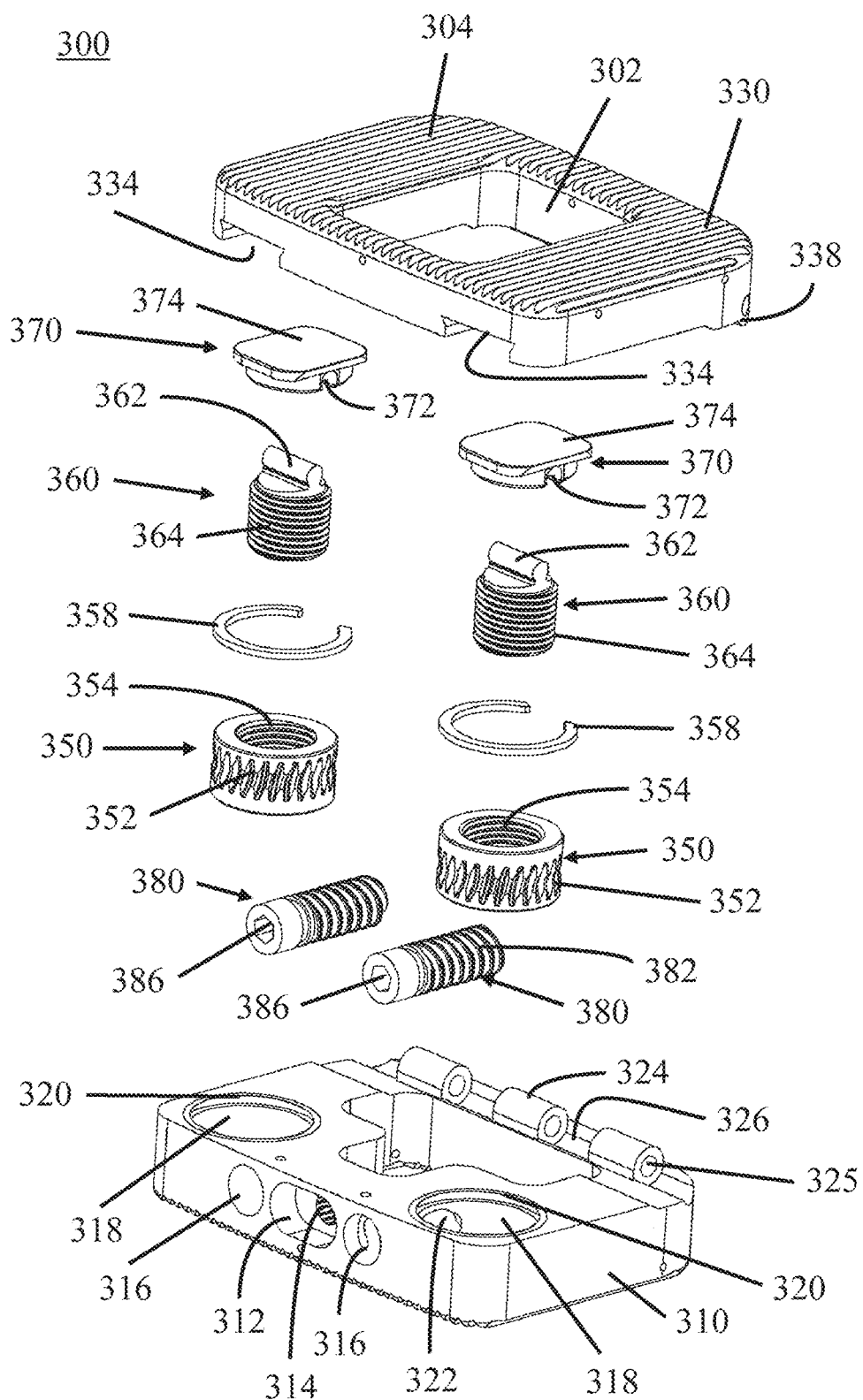
FIG. 18 is an exploded view of the expandable interbody fusion device of FIG. 15, in accordance with an aspect of the present invention.
Figure 19:
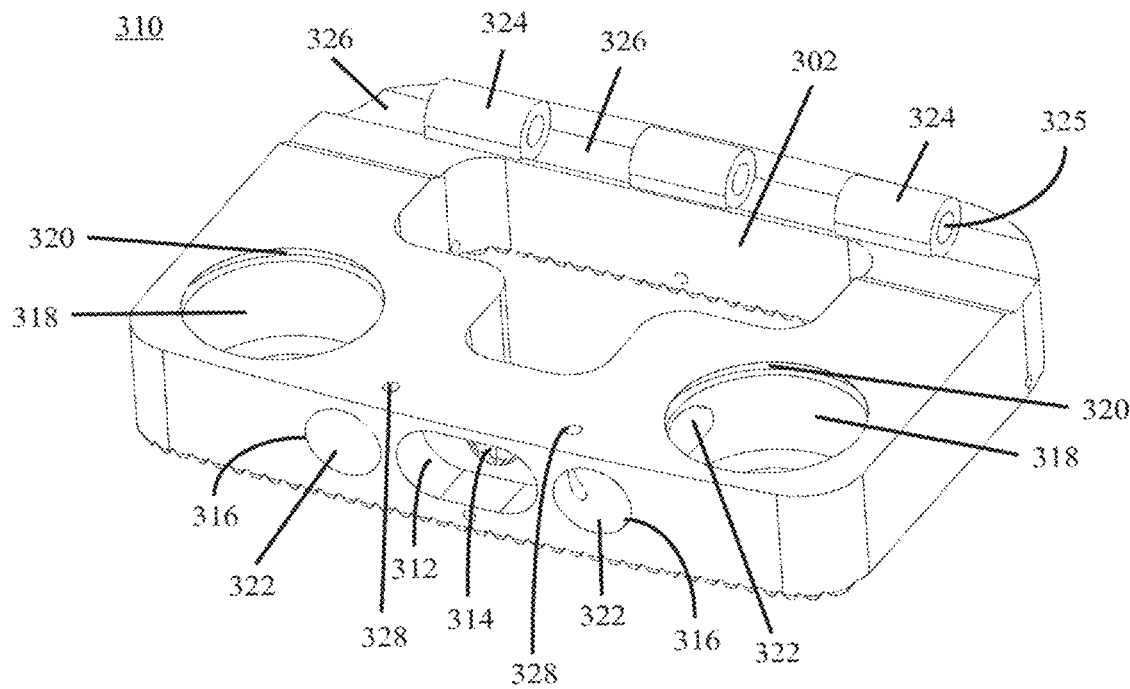
FIG. 19 is a superior perspective view of the expandable interbody fusion device of FIG. 15, showing only the base or bottom member, in accordance with an aspect of the present invention.

As seen in FIGS. 18 and 19, the base member 310 may also include a tool alignment opening 312 on a first lateral side of the base member 310, a tool attachment opening 314 in the tool alignment opening 312, and a first adjustment opening 316 and second adjustment opening 317 on the lateral side of the base member 310 and which may be on opposite sides of the tool alignment opening 312, as seen in FIGS. 15-19. The base member 310 may also include at least one hole or lumen 318 near the proximal and/or distal ends of the base member 310 to house at least one expansion mechanism 340, which will be discussed in greater detail below. In one embodiment, as illustrated in FIGS. 15-23, the base member 310 may include, for example, two holes 318. The holes 318 may be of the type described above with reference to holes 118 of implant 100 and for brevity sake will not be described again here. The base member 310 may also include at least one pivot cylinder 324, at least one hinge channel 326, and at least one opening 328. The at least one pivot cylinder 324 and the at least one hinge channel 326 may alternate as depicted in FIGS. 18 and 19.

Figure 20:
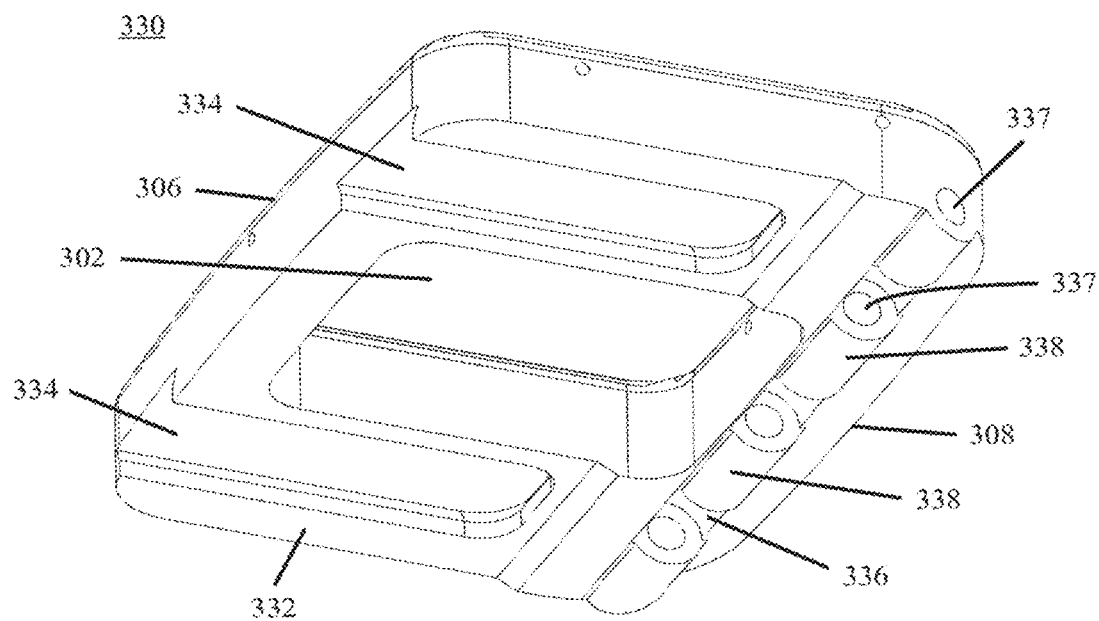
FIG. 20 is an inferior perspective view of the expandable interbody fusion device of FIG. 15, showing only the top or superior member, in accordance with an aspect of the present invention.

As seen in FIGS. 18 and 20, the top or superior member 330 also includes an undersurface 332 with at least one relief area 334 that is adjacent to the central opening 302. The central opening 302 may be configured to permit the insertion of bone graft material into the inner cavity of the implant 300 prior to or after implantation. In one embodiment, as illustrated in FIGS. 15-23, the top member 330 may include, for example, two relief areas 334 which may be of the type described above with reference to relief areas 134 and for brevity sake will not be described again here.

As seen in FIGS. 18-20, the relief areas 334 may be configured to mate with at least one correspondingly shaped load head 370 of the an expansion mechanisms 340. The top member 330 may also include at least one hinge channel 336 and at least one pivot cylinder 338 and the hinge channels 336 may alternate with the pivot cylinders 338, as depicted in FIG. 20. The at least one hinge channel 336 may mate with the at least one pivot cylinder 324 of the base member 310 and the at least one pivot cylinder 338 may mate with the at least one hinge channel 326 of the base member 310 to enable the implant 300 to extend on a first lateral side 306 while remaining closed on a second lateral side 308. A pin 339 may be inserted into openings 325, 337 in the pivot cylinders 324, 338, respectively, to pivotally secure the top member 330 to the base member 310. The pivot cylinders 324 and hinge channels 326 of the base member 310 and the hinge channels 336 and pivot cylinders 338 of the top member 330 allow the hinge channels 326, 336 to pivot or rotate around the outer diameter of the pivot cylinders 324, 338 when the at least one expansion assembly 342 is extended or retracted causing the top member 330 to tilt or slant relative to the base member 330. In another embodiment, the base member 310 may include a pivot cylinder 324 and the top member 330 may include a hinge channel 336, alternatively, the base member 310 may include a hinge channel 326 and the top member 330 may include a pivot cylinder 338.

Figure 21:
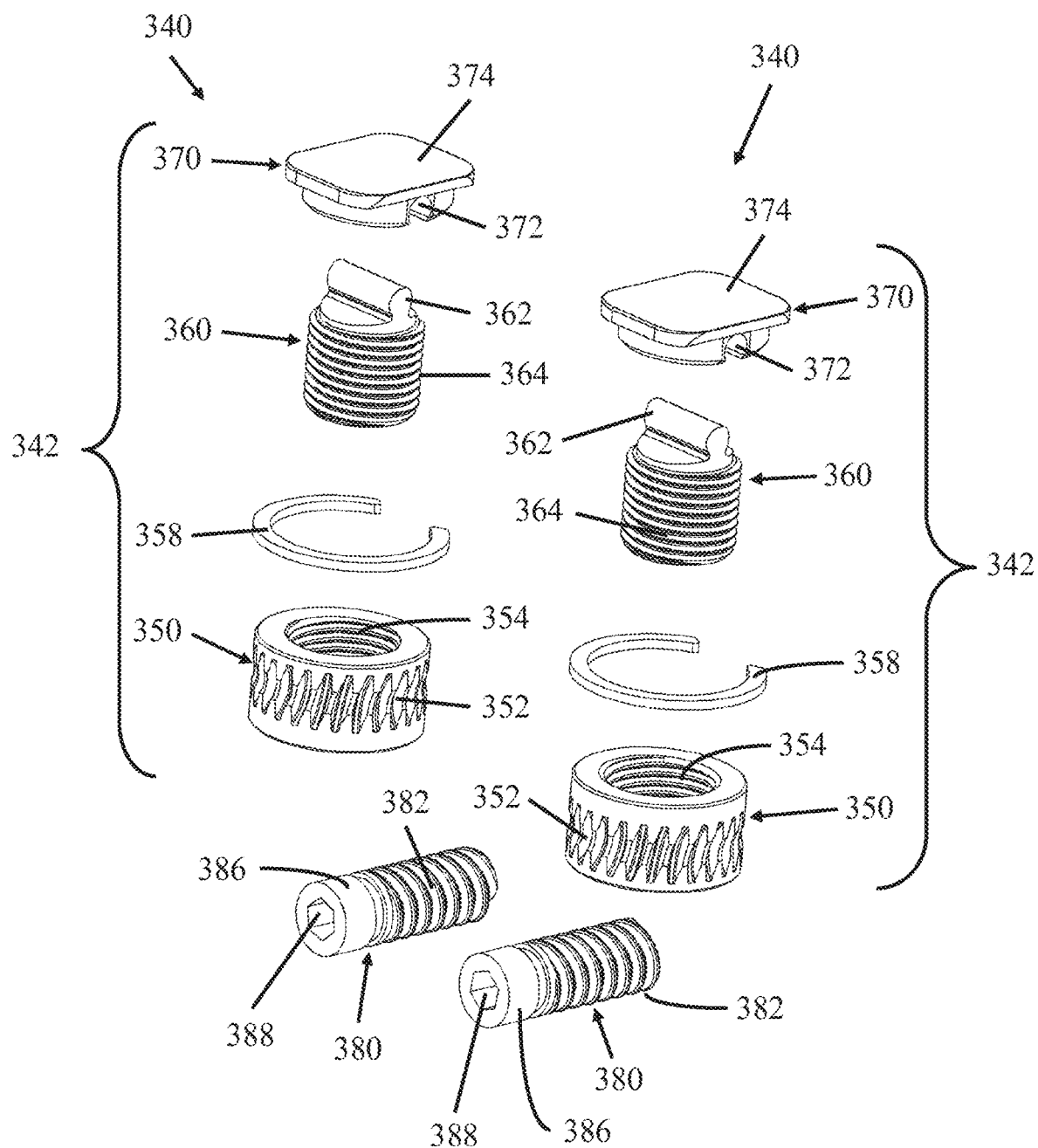
FIG. 21 is an exploded view of the expansion mechanisms of the expandable interbody fusion device of FIG. 15, in accordance with an aspect of the present invention.

Referring now to FIG. 18 with continued reference to FIGS. 19 and 20, an exploded view of all of the components that comprise the implant 300 is shown. As shown in FIG. 21, the two expansion mechanisms 340 of the implant 300 include an expansion assembly 342 and a drive rod 380. The expansion assemblies 342 may include a cylindrical gear 350, a support means 358, a threaded rod 360, and a load head 370. The vertical cylinder or cylindrical gears 350 may be of the type described above with reference to cylindrical gears 150 of implant 100 and for brevity sake will not be described again here.

Figure 22:
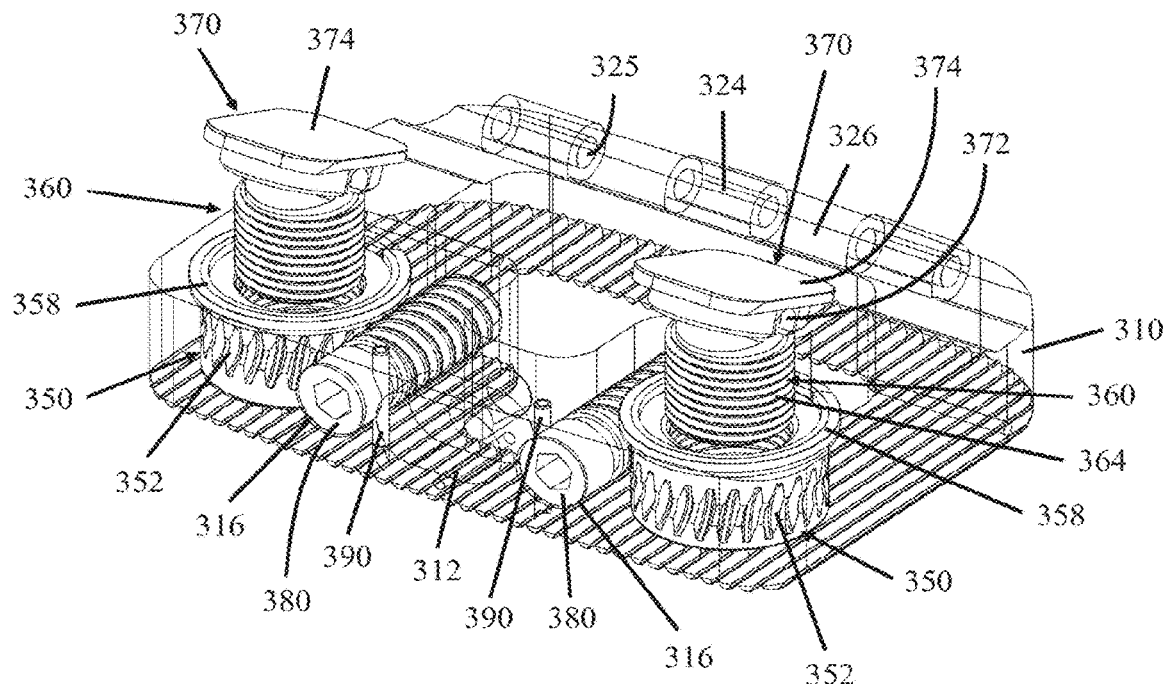
FIG. 22 is a posterior perspective view of the expandable interbody fusion device of FIG. 15 without the top member, showing the expansion assemblies seated in the transparent base member, extended and tilted to accommodate the slanted top member, in accordance with an aspect of the present invention.
Figure 23:
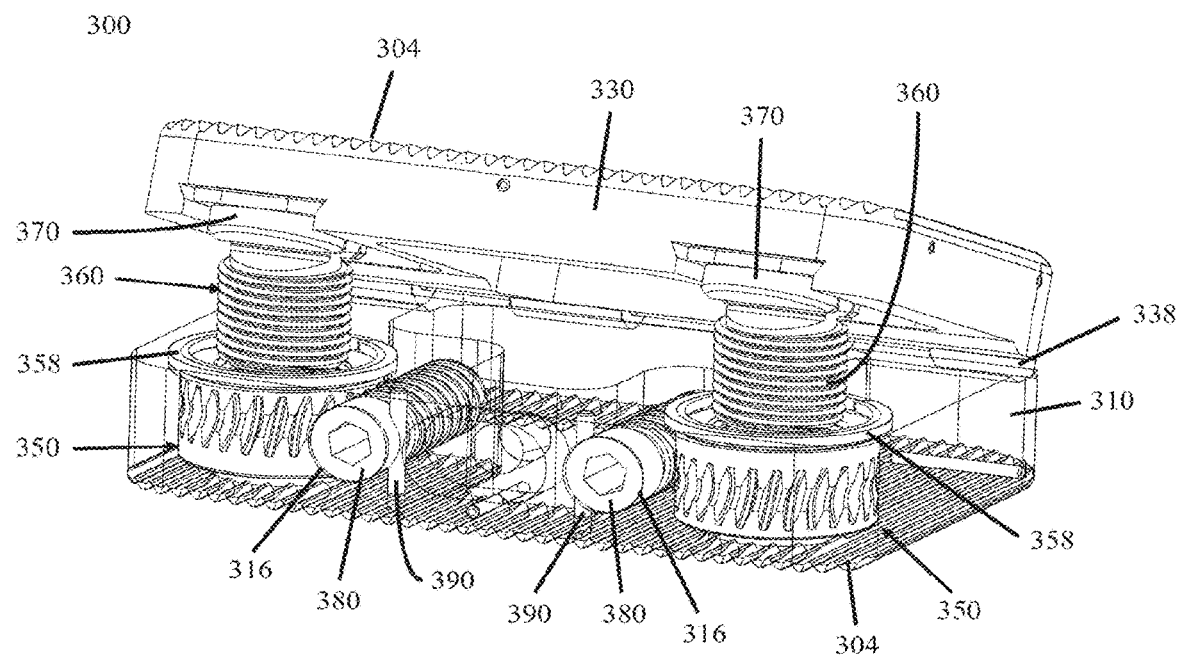
FIG. 23 is a perspective view of the expandable interbody fusion device of FIG. 15 with a transparent base member showing a drive rod and locking mechanism, in accordance with an aspect of the present invention.

As shown in FIG. 22, the support means 358 may sit on the shoulders 320 of the base member 310 and function to maintain the expansion assemblies 342 in a vertical orientation relative to the base member 310 and aligned with the holes 318. The support means 358 may also be used adjacent to the gears 350 and threaded rods 360 and may hold the gears 350 in the holes 318. The support means 358 may be of the type described above with reference to support means 158 of implant 100 and for brevity sake will not be described again here. The shoulders 320 may also operate as bearing surfaces against which the support means 358 contacts to facilitate the rotation of the expansion assemblies 342 when actuated.

As shown in FIGS. 18, 21 and 22, the threaded rods 360 may be of the type described above with reference to the threaded rods 160 of the implant 100 and for brevity sake will not be described again here. The pivot cylinder 362 of the threaded rods 360 may be inserted into a distal channel 372 of the load heads 370. These constructs allow the load heads 370 to pivot, slide, or rotate around the outer diameter of the pivot cylinders 362 when the threaded rods 360 are extended causing the top member 330 to tilt or slant. Tilted or slanted load heads 370 are shown in FIGS. 17 and 22. The load heads 370 may be of the type described above with reference to load heads 170 of the implant 100 and for brevity sake will not be described again here. The reliefs 334 in the undersurface 332 and the correspondingly shaped load heads 370 facilitate the angulation process and the load transfer between the top member 330 and the base member 310 while avoiding potential binding of the expansion assemblies 342 during the expansion and retraction process.

The drive rods 380 of the expansion mechanisms 340 may be inserted into the adjustment openings 316 and sit in the channel 322 of the base member 310, as shown in FIGS. 18, 21, and 22. Each drive rod 380 may include a worm gear 382 and a cylindrical shaft 386. The worm gear 382 may also have a tool opening 388 in an end of the cylindrical shafts 386 for coupling with a tool 400. In addition, the cylindrical shafts 386 may include a channel 376 for mating with a pin 390 to secure the drive rods 380 in the base member 310 to enable adjustment of the top member 330 without the drive rod 380 backing out of the implant 300. The pin 390 may also prevent the drive rod 380 from backing out of the implant 300 after implantation into the patient's spine (See FIG. 23). By placing the adjustment openings 316 and the channels 322 in a side of the implant 300, the worm gears 382 of the drive rods 380, which are inserted into the channels 322, intersect with the holes 318 of the base member 310. The worm gears 382 may be configured to engage with the gears 350 of the expansion assemblies 342 which sit in the holes 318 of the base member 310. FIG. 22 shows the assembled implant 300 without the top member 330 with the drive rods 380 positioned offset from the lateral axis and extending laterally into the base member 310.

Figure 24:
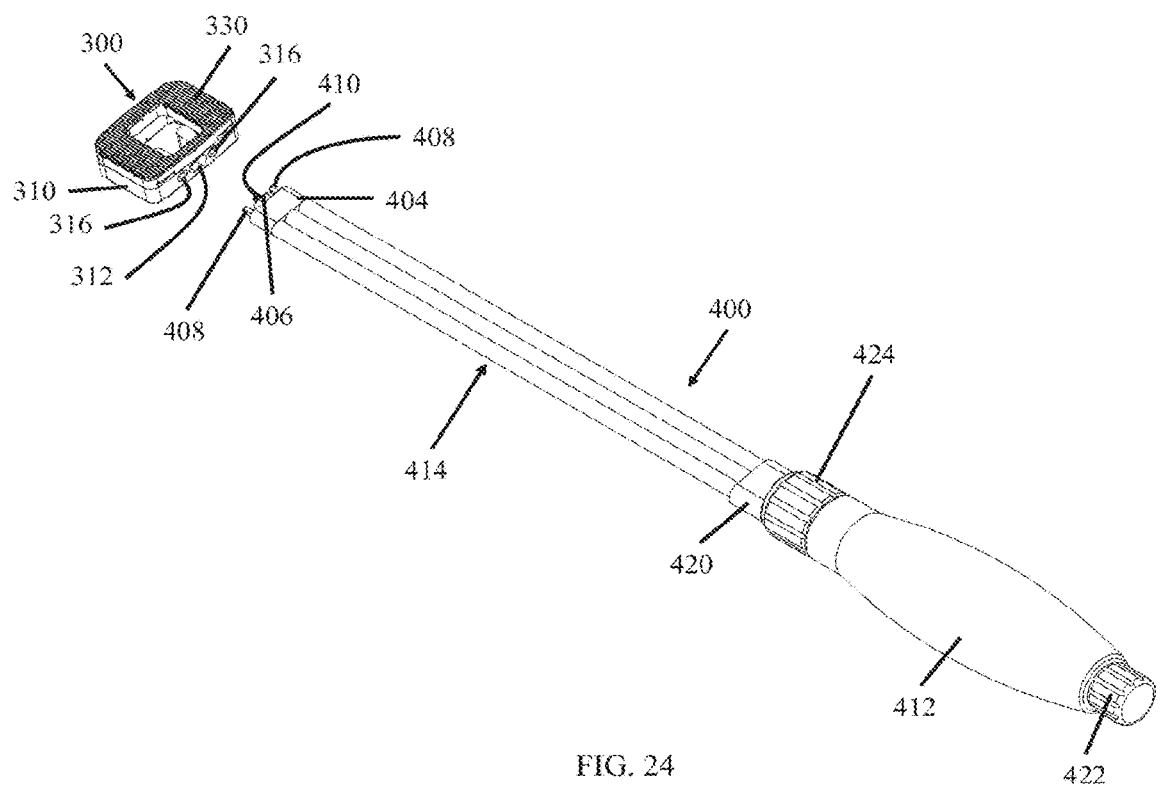
FIG. 24 is a perspective view of the expandable interbody fusion device of FIG. 15 and an expansion tool, in accordance with an aspect of the present invention.
Figure 25:
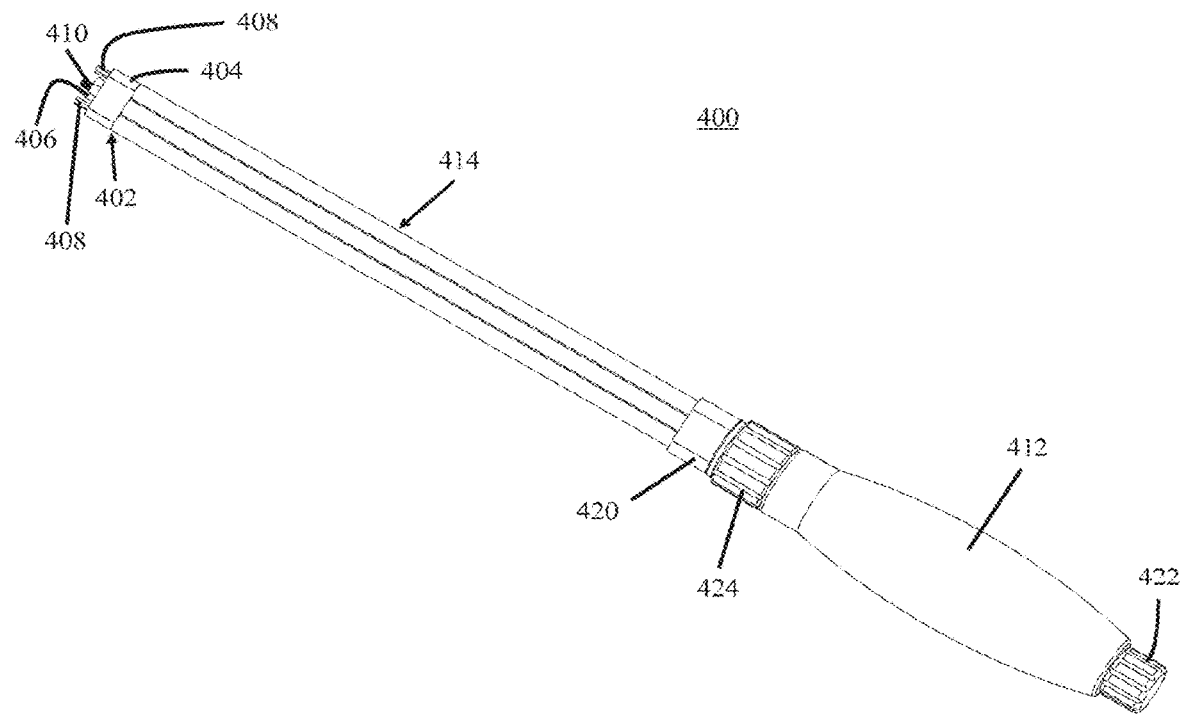
FIG. 25 is a perspective view of the expansion tool of FIG. 24, in accordance with an aspect of the present invention.
Figure 26:
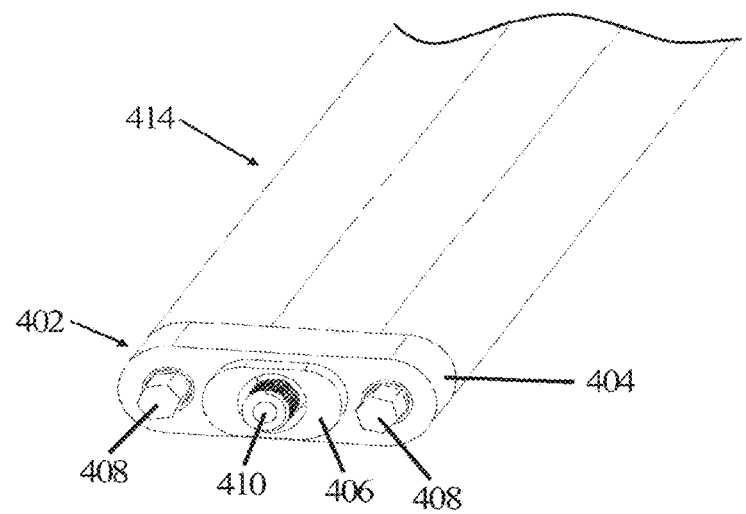
FIG. 26 is a truncated anterior view of the attachment end of the expansion tool of FIG. 24, in accordance with an aspect of the present invention.

When the implant 300 is inserted into a patient using tool 400, as shown in FIG. 24, the tool 400 engages the alignment opening 312, the attachment opening 314 and the adjustment openings 316, as described in greater detail below. Once the implant 300 is inserted into the patient between two vertebrae using the tool 400, the drive rods 380 with the gears 350 function to mirror the rotational movement exerted by the tool 400, described in greater detail below, and translate the movement to the gears 350. The expansion mechanisms 340 function to convert rotation movement of the gears 350 into linear or translational movement of the load heads 370 positioned at the superior end of the threaded rods 360. Rotation of the gears 350 will result in a travel distance of the threaded rods 360 when the expansion mechanisms 340 are actuated by the tool 400. As the gears 350 are coupled to the drive rods 380, the coupled gears 350 will turn as the drive rod 380 is rotated.

With continued reference to FIGS. 15-23, as the drive rods 380 are rotated by the tool 400 the teeth 378 of the worm gears 382 of the drive rods 380 are configured to mate with the substantially vertical depressions 352 of the gears 350. As described above, the expansion assemblies 342 act to covert rotational movement of the gears 350 into translational movement of the threaded rods 360. This is achieved by allowing free rotational movement of the gears 350 while restricting the rotation of the threaded rods 360. By restricting the rotation of the threaded rods 360, the rods translate in either an upward or downward direction relative to the gears 350 depending upon whether the threads (external and internal) 354, 364 are oriented in a right-handed or left-handed direction. As discussed above, when the threaded rods 360 move, the load heads 370 contact the relief areas 334 of the undersurface 332 of the top member 330 to either move it away from or towards the base member 310. In other words, the bone contacting surface 304 of the top member 330 will be angled relative to the base member 310 depending on the rotational direction of the tool 400. Locking mechanisms, for example, the locking mechanism 192 of FIG. 10, which will not be described again here for brevity sake, may be inserted into adjustment openings 316 to secure the implant 100 in the desired expansion or refraction.

Referring now to FIGS. 24-35, a tool 400 for inserting the implant 300 into a patient is shown. The tool 400 is designed to engage the expansion mechanisms 340. The insertion end 402 of the tool 400 may be configured with a housing 404 including a protrusion 406 shaped to correspond to the alignment opening 312 in the base member 310. The insertion end 402 may also include at least one adjustment mechanism 408 and a securement mechanism 410 which protrude out of the distal end of the housing 404. The adjustment mechanisms 408 may be configured, for example, to have a hex male head, square, or other multi-lobed configuration that will allow for the user to rotate the knob 424 of the tool 400 and cause the expansion mechanisms 340 to rotate. The securement mechanism 410 may be configured, for example, to include threads for engaging corresponding threads in the attachment opening 314.

Opposite the insertion end 402, the tool 400 has a handle 412 which may be connected to the housing 404 of the insertion end 402 by at least one tube 414. In one embodiment, there are three tubes 414, a center tube 414 for the securement mechanism 410 and two lateral tubes 414 for the adjustment mechanisms 408. The at least one tube 414 may be coupled to the housing 404 on the distal end and secured to an attachment member 420 which couples to the handle 412 at the proximal end by fasteners, for example, screws. The securement mechanism 410 may extend from the handle 412 to the housing 404 inside the center tube 414. In addition, the adjustment mechanisms 408 may also extend between the housing 404 and the handle 412 inside the tubes 414 adjacent to the center tube 414 with the securement mechanism 410.

Figure 27:
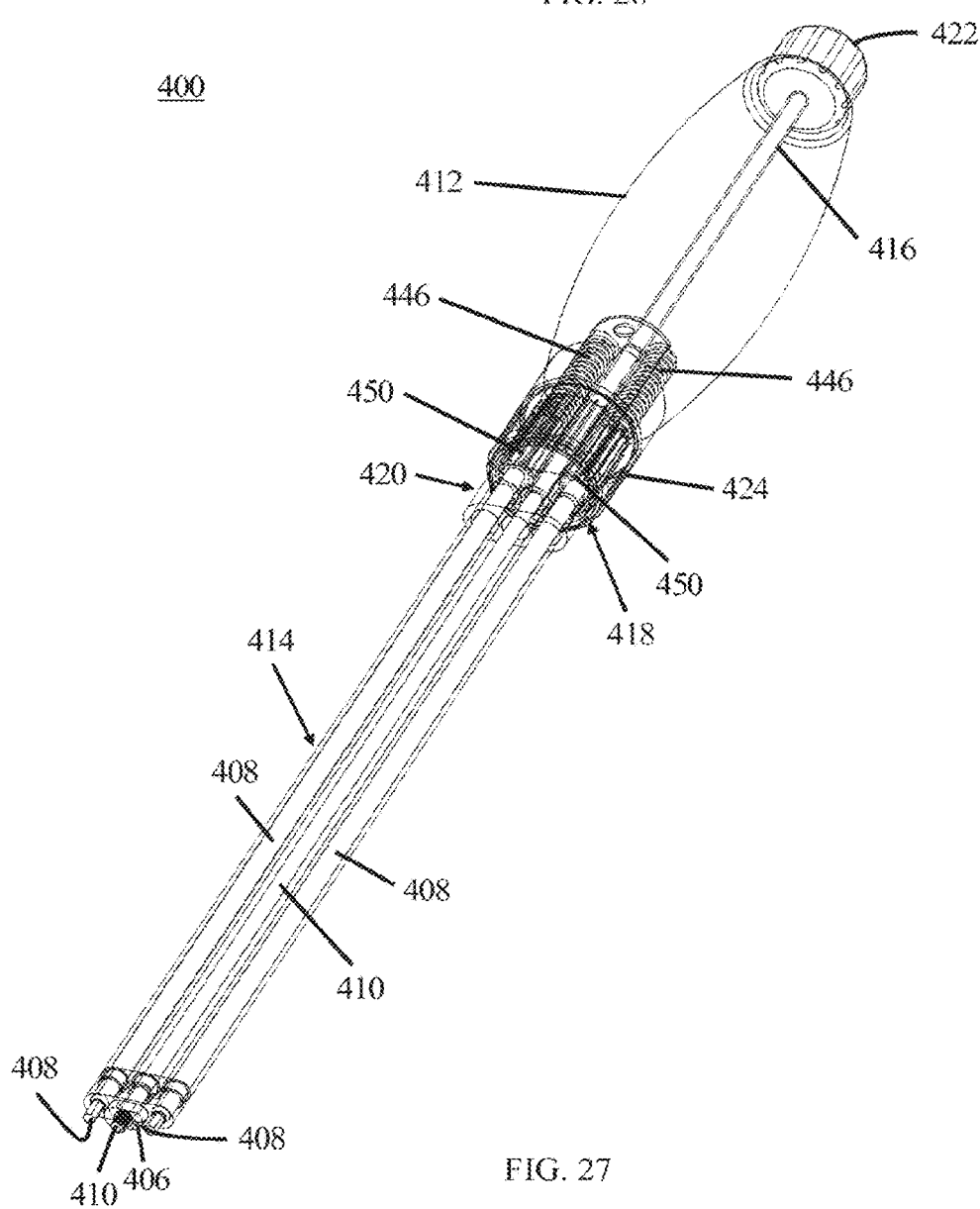
FIG. 27 is a perspective view of the expansion tool of FIG. 24 with a transparent outer housing, in accordance with an aspect of the present invention.
Figure 28:
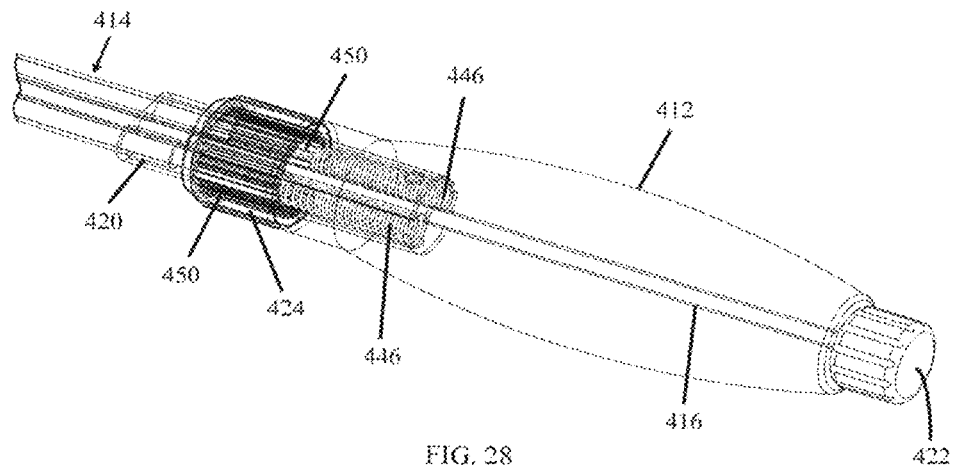
FIG. 28 is a truncated distal view of the handle end of the expansion tool of FIG. 24 with a transparent outer housing, in accordance with an aspect of the present invention.
Figure 29:
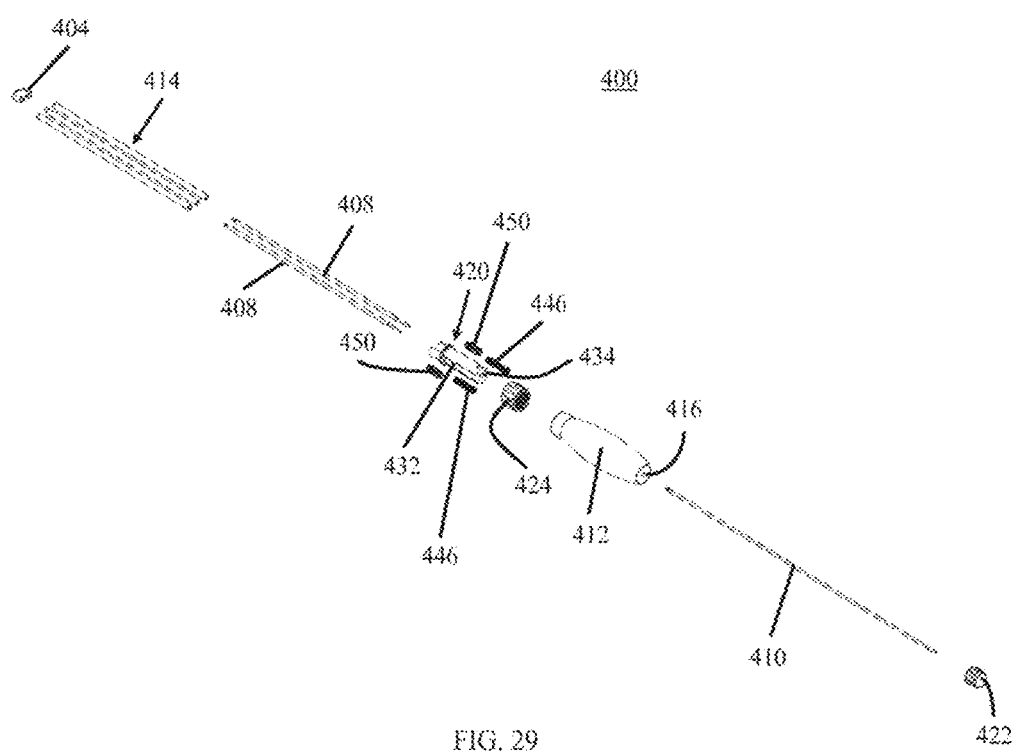
FIG. 29 is an exploded view of the tool of FIG. 24, in accordance with an aspect of the present invention.
Figure 30:
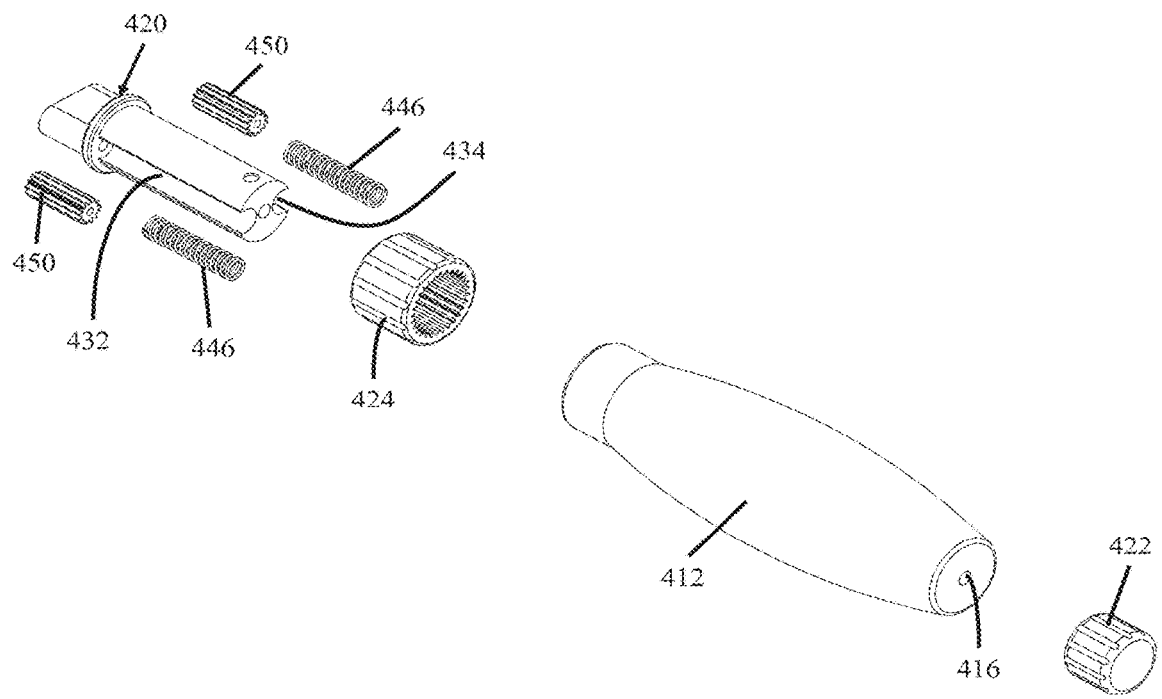
FIG. 30 is an exploded view of the handle portion of the tool of FIG. 24, in accordance with an aspect of the present invention.
Figure 31:
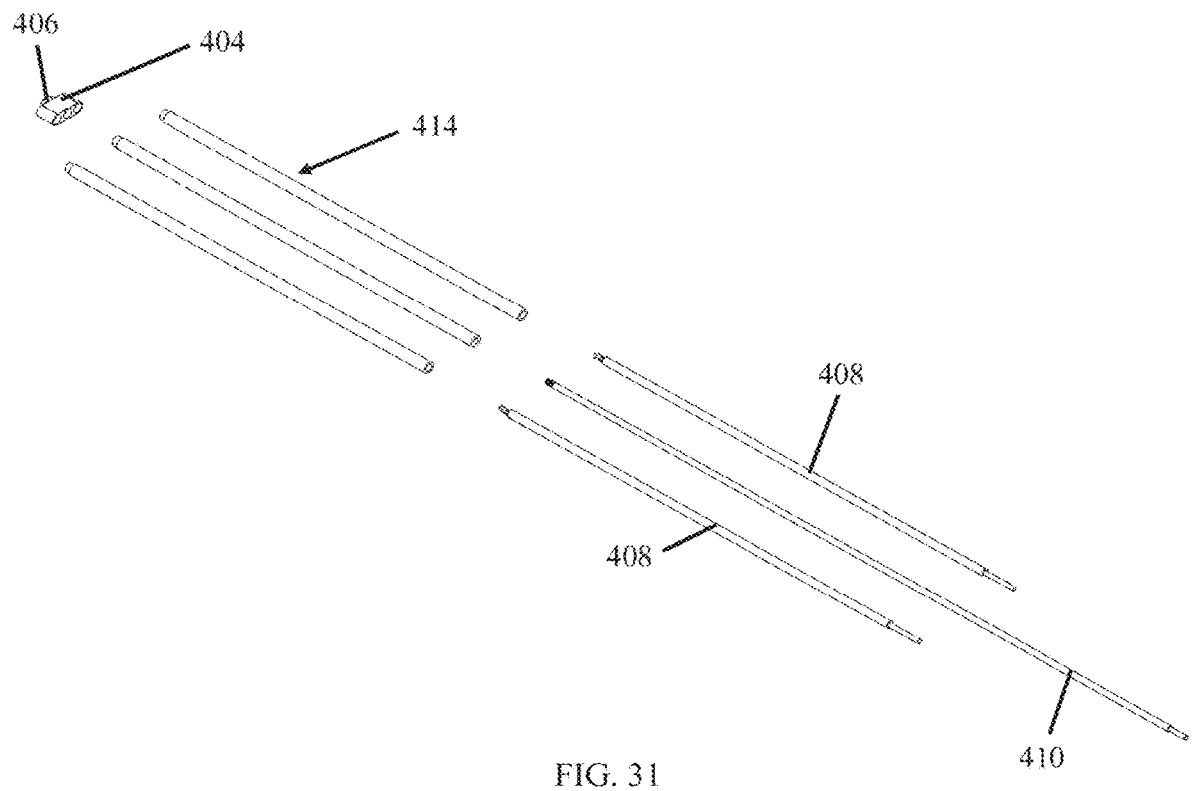
FIG. 31 is an exploded view of the insertion portion of the tool of FIG. 24, in accordance with an aspect of the present invention.
Figure 32:
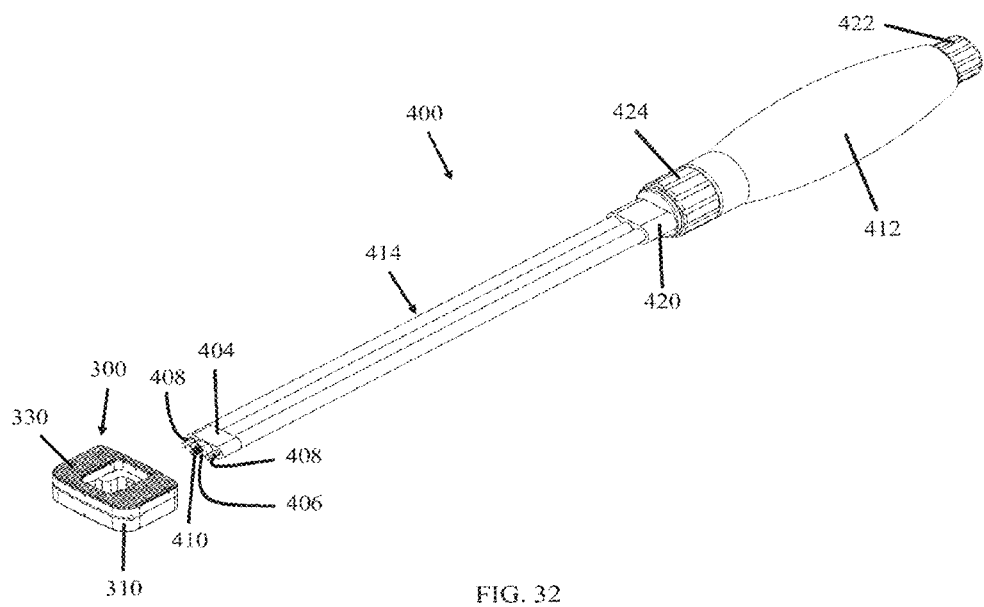
FIG. 32 is a perspective view of the expandable interbody fusion device of FIG. 15 and the tool of FIG. 24, in accordance with an aspect of the present invention.
Figure 33:
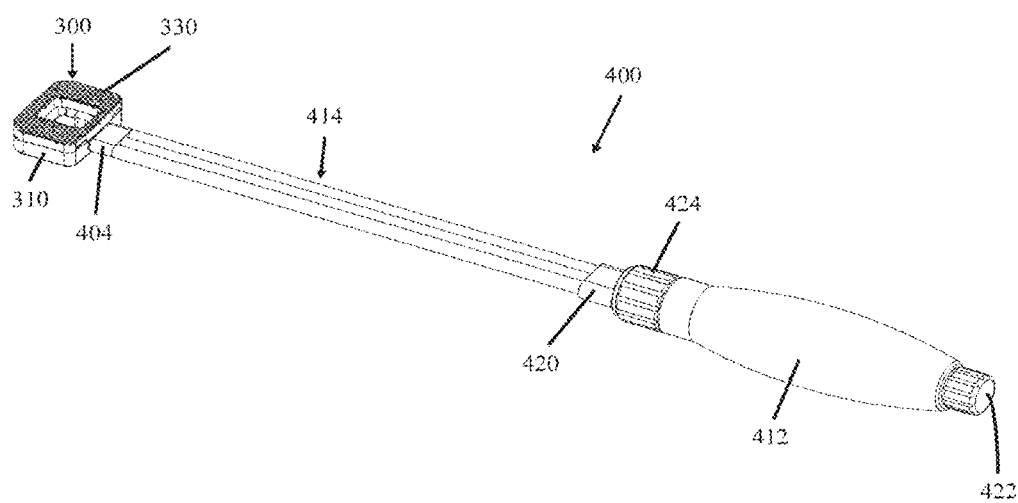
FIG. 33 is a perspective view of the tool of FIG. 24 engaging the expandable interbody fusion device of FIG. 15, in accordance with an aspect of the present invention.
Figure 34:
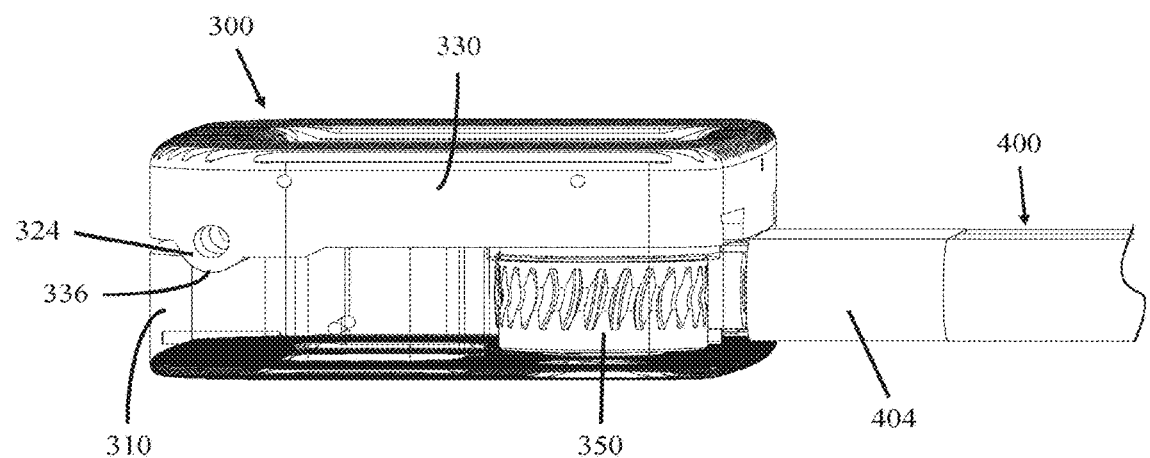
FIG. 34 is a truncated view of the tool of FIG. 24 inserted into the implant of FIG. 15, in accordance with an aspect of the present invention.
Figure 35:
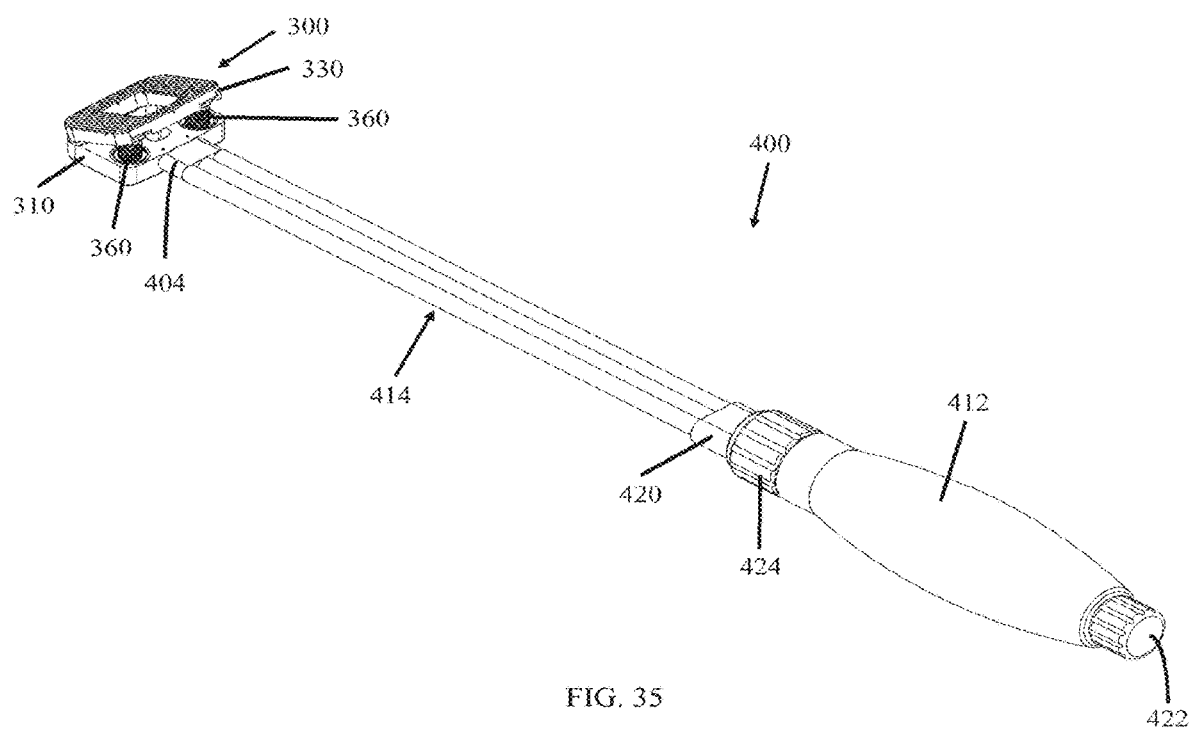
FIG. 35 is a perspective view of the tool of FIG. 24 engaging the expandable interbody fusion device of FIG. 15 in an expanded position, in accordance with an aspect of the present invention.

As seen in FIGS. 27-29, the handle 412 of the tool 400 may also include a first opening 416 along the longitudinal axis of the handle 412 and a second opening 418 extending into the handle 412 from the distal end. The handle 412 may also include a first knob 422 and a second knob 424. The first knob 422 may engage the securement mechanism 410 at a proximal end and the distal end of the securement mechanism 410 may be inserted into the opening 416 in the handle 412. The second knob 424 may engage an attachment member 420 which in turn may be inserted into a portion of the handle 412 through opening 418. The attachment member 420 may include two grooves 432, 434, each groove 432, 434 mates with two gears 450 and two spring mechanisms 446. The gears 450 may fit into the grooves 432, 434 and a spring 446 may sit on the proximal end of the gears 450, the knob 424 may fit over the springs 446 and gears 450 to couple the exterior grooves of the gears 450 with the interior grooves of the knob 424. The attachment member 420 may then be inserted into the handle 412 and secured. The adjustment mechanisms 408 may engage the distal end of the gears 450 to enable rotation of the adjustment mechanisms 408 by rotating the knob 424.

During use a surgeon may insert the tool 400 into the implant 300 by aligning the protrusion 406 of the insertion end 402 of the tool 400 with the alignment opening 312 of the implant 300. Once the tool 400 and implant 300 are aligned, the securement mechanism 410 may be coupled at a proximal end to the knob 422. The securement mechanism 410 may then be inserted into the opening 416. The securement mechanism 410 may be advanced through the handle 412, the attachment member 420, and the tube 414 until the distal end of the securement mechanism 410 extends out of the housing 404. The knob 422 of the tool 400 may be rotated which in turn will rotate the securement mechanism 410. As the knob 422 rotates the securement mechanism 410, the distal end of the securement mechanism 210 engages the threads 308 of the attachment opening 314 of the implant 300. The securement mechanism 410 of the tool will couple with the attachment opening 314 of the implant 300 to secure the implant 300 to the tool 400 for insertion into a patient. In addition, as the securement mechanism 410 engages the attachment opening 314 of the implant 300, the adjustment mechanisms 408 of the tool will engage the openings 386 in the drive rods 380 of the implant 300.

Once the implant 300 is secured to the tool 400, the implant 300 may then be inserted into the desired position in the patient. The physician may then rotate the knob 424 which in turn will rotate the distal ends of the adjustment mechanisms 208. As the knob 424 is rotated, the adjustment mechanisms 408, which are coupled to the openings 386 in the drive rods 380, engages the expansion mechanisms 340 and expands the near side of the implant 300 to angle the top member 330 relative to the base member 310. The cogs or teeth 378 of the worm gears 384 on the end of the drive rods 380 are sized to mate with the corresponding serial depressions 352 of the gears 350 to facilitate rotation of the gears 350 when the knob 424 of the tool 400 is turned. Once the desired expansion of the implant 300 is achieved, the tool 400 may then be removed from the patient.

The tool 400 may be removed from the patient by rotating the knob 422 to disengage the distal end of the securement mechanism 410 from the attachment opening 314 of the implant 300. As the securement mechanism 410 rotates it disengages the attachment opening 314 and the protrusion 406 and the adjustment mechanisms 408 of the insertion end 402 of the tool 400 may slide out of the alignment opening 412 and adjustment openings 416, respectively. After the tool 400 is removed from the implant 300, locking mechanisms, for example, locking mechanism 192 as shown in FIG. 10 may be inserted into the openings 316 to lock the implant 300 in the desired expansion or refraction. It is also contemplated that the above method for inserting the implant 300 using tool 400 may be performed in alternative orders.

Figure 36:
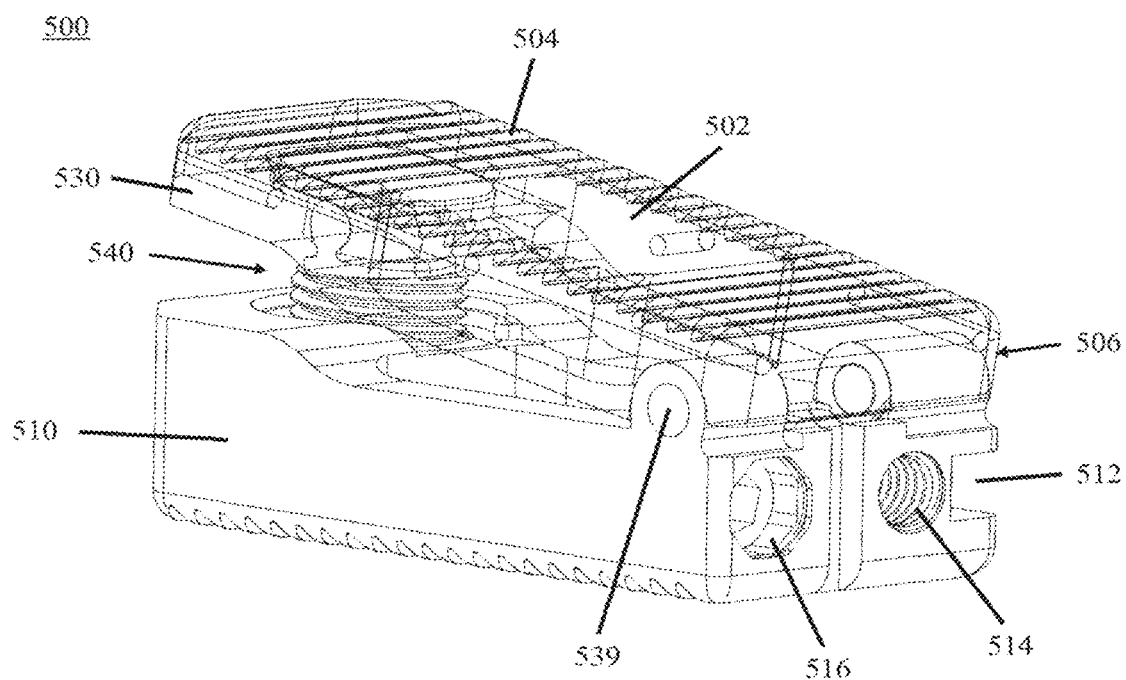
FIG. 36 is an isometric view of an expandable interbody fusion device with a transparent top member and the moveable member extended, in accordance with an aspect of the present invention.
Figure 37:
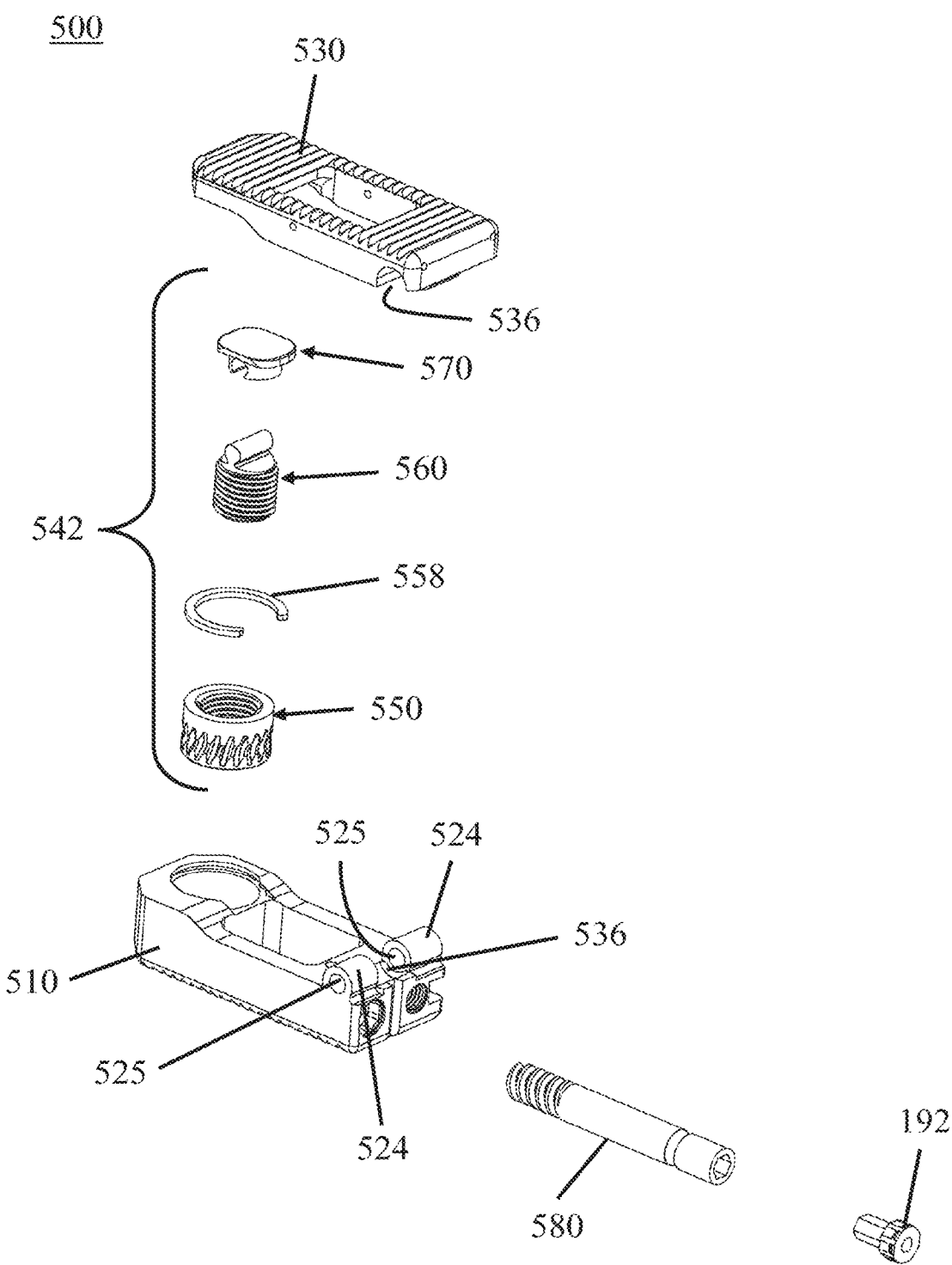
FIG. 37 is an exploded superior view of the expandable interbody fusion device of FIG. 36, in accordance with an aspect of the present invention.
Figure 38:
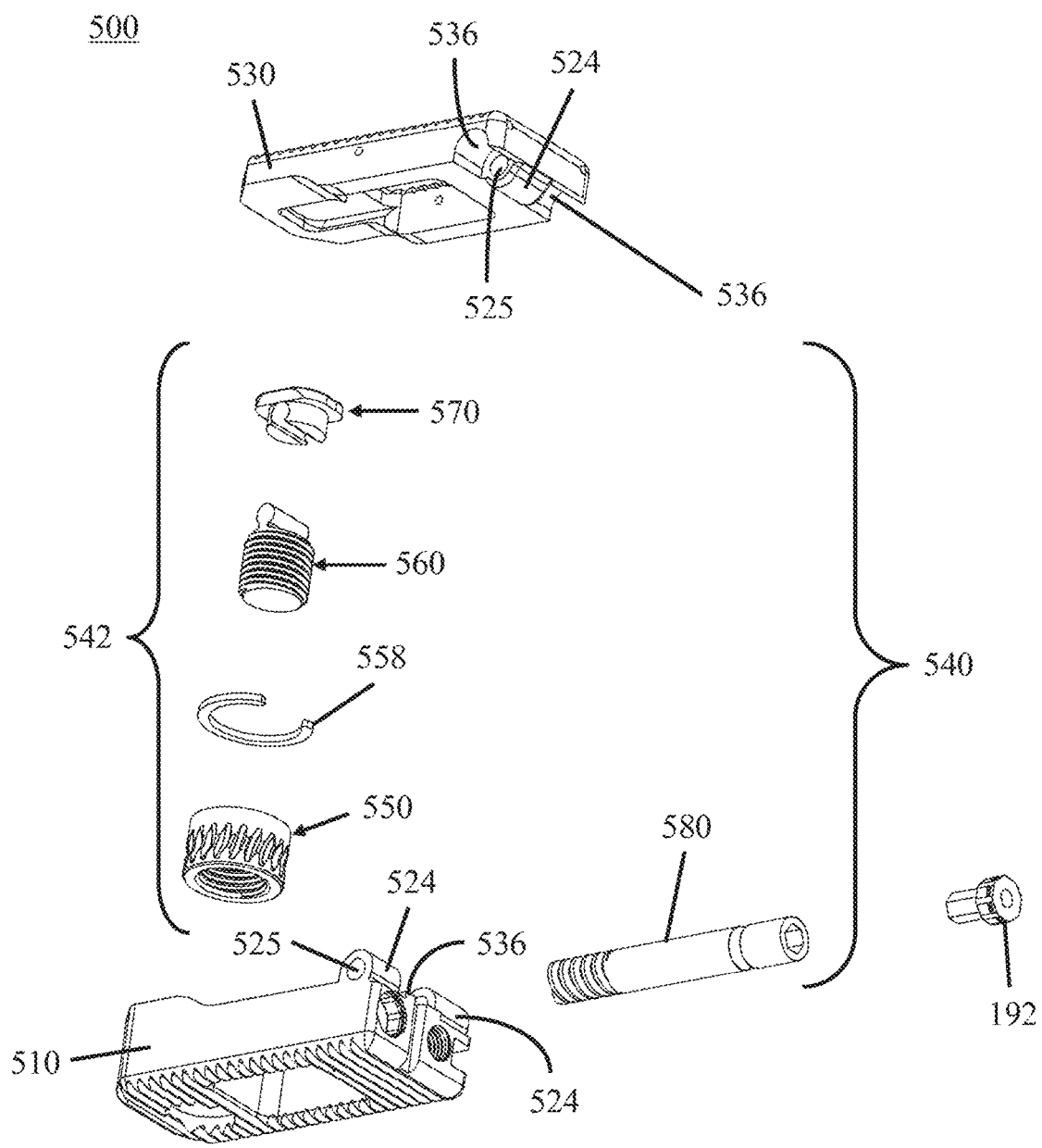
FIG. 38 is an exploded inferior view of the expandable interbody fusion device of FIG. 36, in accordance with an aspect of the present invention.

Referring now to FIGS. 36-38, an adjustable interbody fusion device 500, is shown and includes a base member 510, at least one moveable top member 530, and at least one expansion mechanism 540. The device 500 is of the type described in U.S. Application No. 61/756,048 filed Jan. 24, 2013, which is herein incorporated by reference in its entirety. An alternative embodiment hinge mechanism 506 including at least one pivot cylinder 524 and at least one hinge channel 536 is shown in FIGS. 36-38. As shown, the hinge mechanism 506 includes at least one pivot cylinder 524 and at least one hinge channel 536 in the base member 510 and at least one pivot cylinder 524 and at least one hinge channel 536 in the top member 530. The at least one hinge channel 536 of the top member 530 may mate with the at least one pivot cylinder 524 of the base member 510 and the at least one pivot cylinder 524 of the top member 530 may mate with the at least one hinge channel 536 of the base member 510 to enable the implant 500 to extend on a far end while remaining closed on a near end. A pin 539 may be inserted into openings 525 in the pivot cylinders 524, to pivotally secure the top member 530 to the base member 510. The pivot cylinders 524 and hinge channels 536 of the base member 510 and the hinge channels 536 and pivot cylinders 524 of the top member 530 allow the hinge channels 536 to pivot or rotate around the outer diameter of the pivot cylinders 524 when the at least one expansion assembly 542 is extended or retracted causing the top member 530 to tilt or slant relative to the base member 530. The expansion mechanism 540 of the implant 500 includes at least one expansion assembly 542 and a drive rod 580. The expansion assembly 542 may include a cylindrical gear 550, a support means 558, a threaded rod 560, and a load head 570. The cylindrical gear 550, support means 558, threaded rod 560, and load head 570 are of the type described above with reference to implants 100 and 300. A locking mechanism 192, of the type described above with reference to FIG. 10, may be inserted into opening in the drive rod 580 to secure the expansion assembly 542 in place to maintain a desired expansion or retraction of the implant 500.

Figure 39:
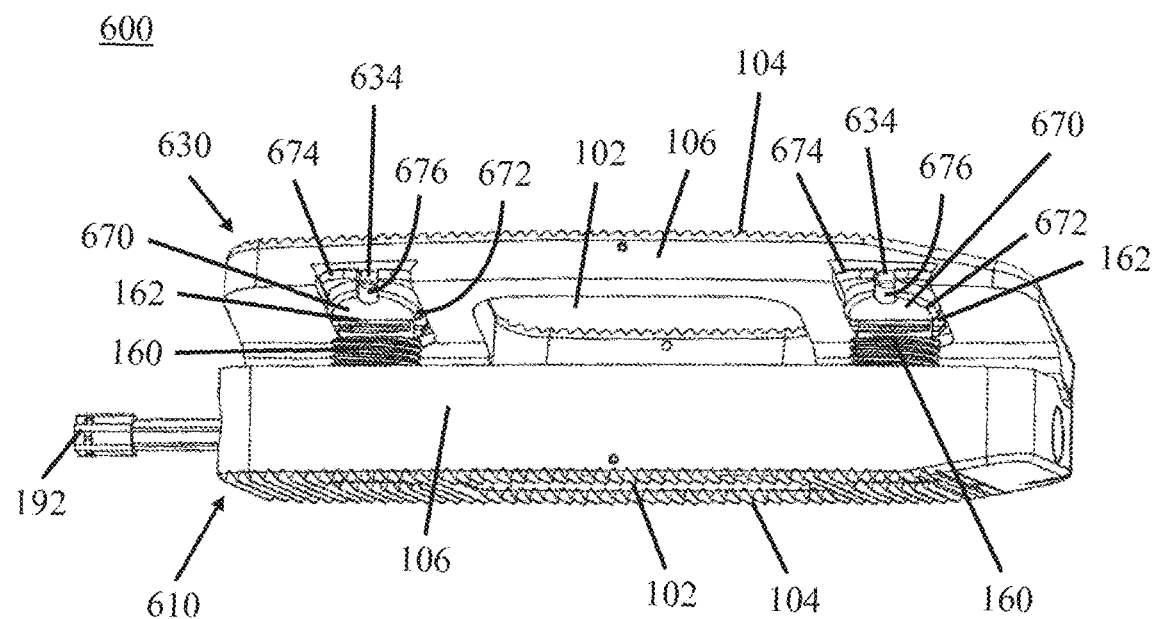
FIG. 39 is a perspective view of a partially open expandable interbody fusion device, in accordance with an aspect of the present invention.
Figure 40:
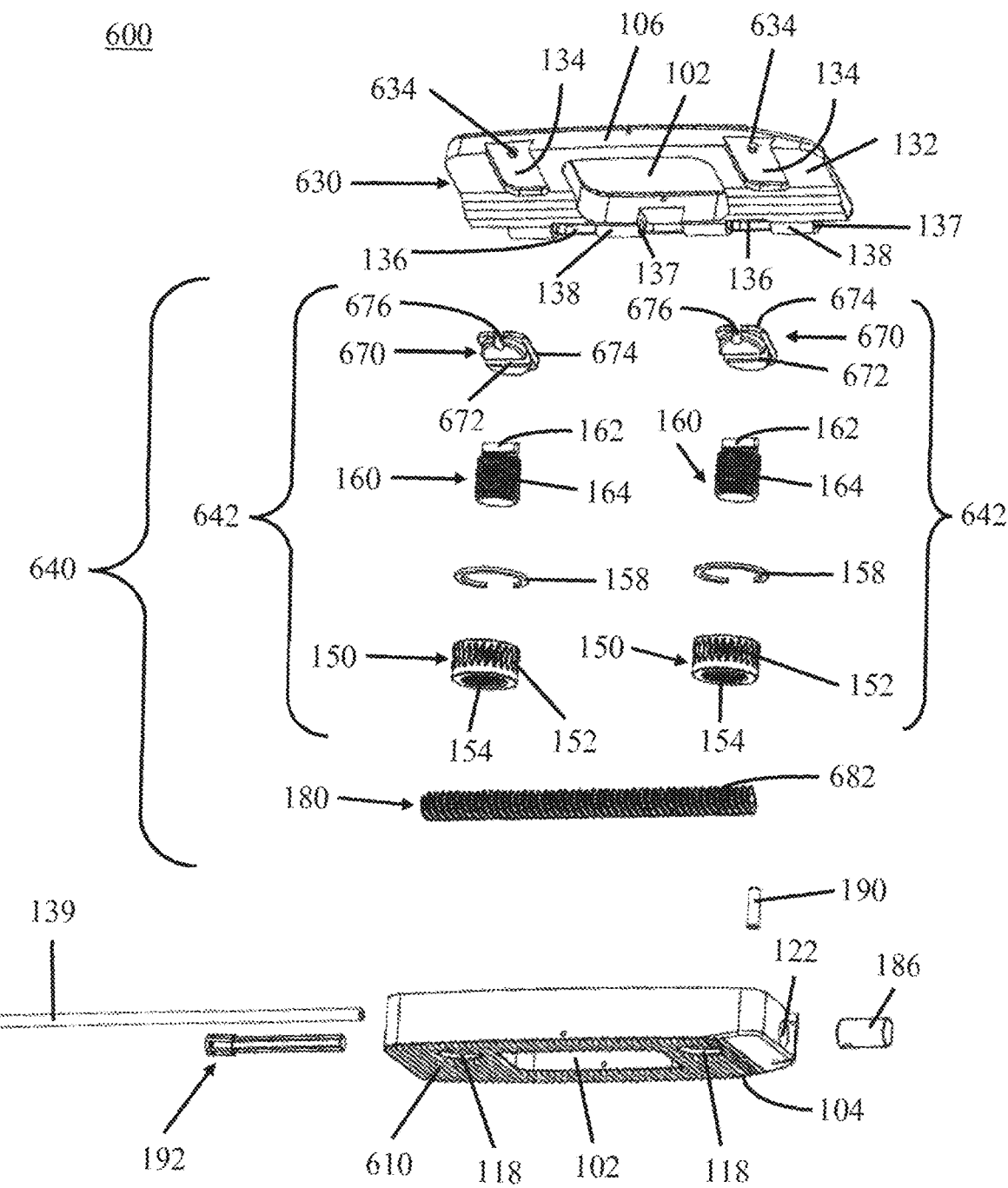
FIG. 40 is an exploded view of the expandable interbody fusion device of FIG. 39, in accordance with an aspect of the present invention.
Figure 41:
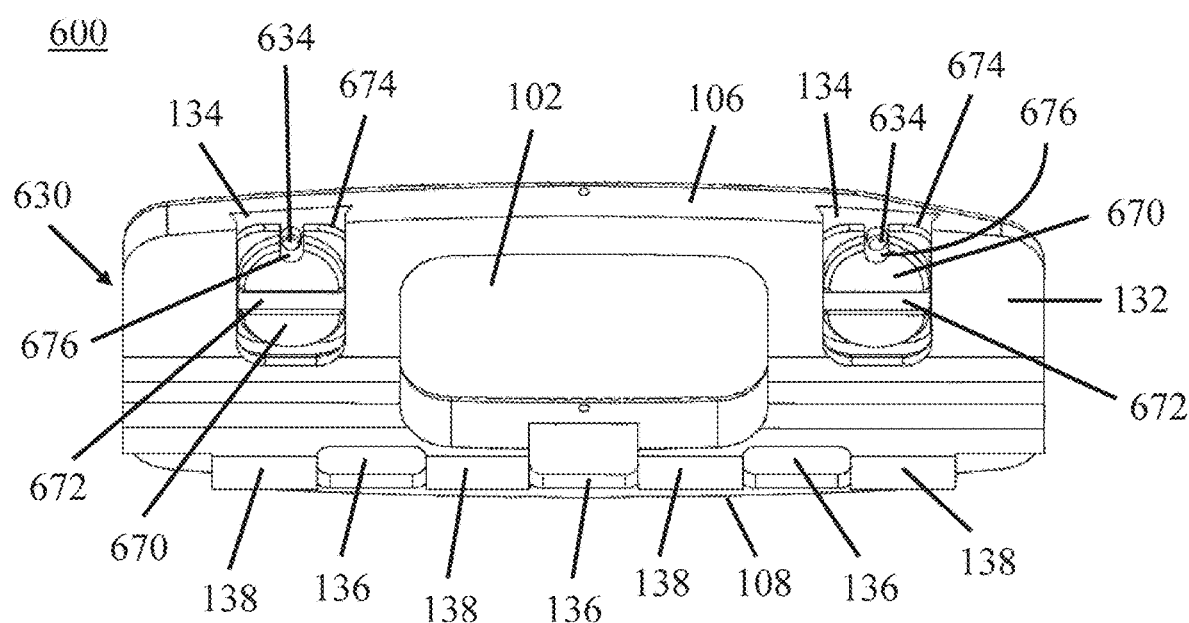
FIG. 41 is an inferior perspective view of the expandable interbody fusion device of FIG. 39, showing only the top or superior member, in accordance with an aspect of the present invention.

Referring now to FIGS. 39-41, an adjustable interbody fusion device 600, is shown and includes a base member 610, at least one moveable top member 630, and an expansion mechanism 640. The base member 610 may be of the type described above with reference to base member 110 which will not be described again here for brevity sake. As shown in FIG. 39, the expansion mechanism or movement mechanism 640 allows a user to angle or raise one side of the bone contacting surface 104 of the top member 630 relative to the bone contacting surface 104 of the base member 610, wherein the near side is expanded and the far side remains engaged or hinged. The bone contacting surfaces 104 of the device 600 are the same as the bone contacting surfaces 104 as described above with reference to device 100, which will not be described again here for brevity sake.

The top or superior member 630, as shown in FIGS. 39-41, may be similar to the top member 130 as described in greater detail above and only the changed features will be described here for brevity sake. The top member 630 may include at least one relief area 134 on the undersurface 132 of the top member 630, as described above with reference to FIGS. 4 and 6. In the depicted embodiment there are two relief areas 134, although one relief area 134 and more than two relief areas 134 are also contemplated. The relief areas 134 may extend from an intermediate position on the undersurface 132 of the top member 630 to at least one outer side of the top member 630. As shown in FIGS. 39-41, the at least one relief area 134 may also include at least one stop pin 634. The stop pin 634 may be positioned closer to the first lateral side 106 than to the second lateral side 108 of the relief area 134 on the undersurface 132 of the top member 630. The stop pin 634 may be an integral portion of the top member 630 or alternatively, the stop pin 634 may be removable. If a removable stop pin 634 is used the relief areas 134 may each include an opening (not shown) for receiving the stop pin 634. A removable stop pin 634 may be secured into the opening (not shown) on the undersurface 132 of the top member 630 by, for example, threads, an adhesive, press-fitting, and the like. The stop pin 634 may protrude or extend out from a surface of the relief area 134 to engage a load head 670, which will be described in greater detail below, and prevent it from sliding out of the relief area 134.

The expansion mechanism 640 of the implant 600, as shown in FIG. 40, may include at least one expansion assembly 642 and a drive rod 180. The expansion assemblies 642 may include a cylindrical gear 150, a support means 158, a threaded rod 160, and a load head 670. The cylindrical gear 150, support means 158, and threaded rod 160 may be of the type described above with reference to device 100 and will not be described again here for brevity sake. The load head 670 may be similar to load head 170 as described above with reference to device 100. The load head 670 may include a distal channel 672 which may receive the pivot cylinder 162 of the threaded rods 160. The load heads 670 may also include superior head surfaces 674 that may be shaped to mate with the corresponding relief areas 134 on the undersurface 132 of the top member 630. The superior head surfaces 674 may also include a cutout 676 shaped to receive the stop pins 634. When the load heads 670 are positioned in the relief areas 134, the cutout 676 may be positioned toward the first lateral side 106 of the top member 630. The superior head surfaces 674 are configured to slide within the reliefs 134 of the undersurface 132, if necessary, to allow the expansion assemblies 642 to lengthen to create the angled relationship of the top member 630 relative to the base member 610. The stop pins 634 are positioned in the relief areas 134 to engage the cutouts 676 in the load heads 670 to prevent the load heads 670 from sliding out of the relief areas 134 while the top member 630 is expanded or retracted relative to the base member 610. The cutouts 676 may have, for example, a relatively circular shape to correspond to the circular shape of the stop pins 634, although alternative shapes for the cutouts 676 and stop pins 634 are also contemplated.

The drive rod 180 of the expansion mechanism 140, as shown in FIG. 40, may include at least one worm gear 682 and a cylindrical shaft 186. The cylindrical shaft 186 may be of the type described above with reference to device 100 and which will not be described again here for brevity sake. The at least one worm gear 682 may be similar to the worm gears 182 and 184 as described above with reference to device 100 and only the differences will be described here for brevity sake. The worm gear 682 of device 600 will have a length essentially the same size as the combined length of worm gears 182, 184. The length of the worm gear 682 will enable engagement with both gears 150 of the expansion assemblies 142 simultaneously. The worm gear 682 may be a monolithic rod that extends along the length of the bottom member 610. In an alternative embodiment, the drive rod 180 may be a monolithic rod extending along the length of the bottom member 610 in channel 122.

The stop pins 634 may also be used in the top members 130, 330 of the devices 100, 300 shown in FIGS. 4 and 18. In addition, cutouts 676 may be formed in the load heads 170, 370 of the devices 100, 300 to receive the stop pins 634 of the top members 130, 330. Further, if the top member 530 of device 500, as shown in FIG. 38, was altered such that the relief area of top member 530 extended all the way to the side of the device 500, then a stop pin 634 may be used in the top member 530 along with a cutout 676 in the load head 570 to prevent the load head 570 from sliding out of the relief area of the top member 530 as the top member 530 is tilted relative to the base member 510.

A surgical method for maintaining a space between two vertebral bodies in a spine may include: obtaining a medical device 100, 300, 500, 600. The medical device 100, 300, 500, 600 including a body member 110, 310, 510, 610 with at least one pivot cylinder 124, 324, 524 and at least one hinge channel 126, 326, 536, a moveable member 130, 330, 530, 630 with at least one pivot cylinder 138, 324, 524 and at least one hinge channel 136, 326, 536, wherein the at least one pivot cylinder 124, 324, 524 of the body member 110, 310, 510, 610 engages the at least one hinge channel 136, 326, 536 of the moveable member 130, 330, 530, 630 and the at least one pivot cylinder 138, 324, 524 of the moveable member 130, 330, 530, 630 engages the at least one hinge channel 126, 326, 536 of the body member 110, 310, 510, 610, and at least one movement mechanism 140, 340, 542, 640 engaging the moveable member 130, 330, 530, 630 and the body member. The method also including inserting and coupling a tool into at least two openings within the medical device 100, 300, 500, 600, slidingly inserting the medical device 100, 300, 500, 600 into a space between two vertebral bodies, and adjusting the tool to move a first side of the moveable member 130, 330, 530, 630 in a vertical direction relative to the body member 110, 310, 510, 610. Coupling the tool into at least two openings within the medical device 100, 300, 500, 600 may include securing the securement mechanism into the at least two openings in the medical device 100, 300, 500, 600. Adjusting the tool to move the first side of the moveable member 130, 330, 530, 630 in a vertical direction relative to the body member 110, 310, 510, 610 may include turning the at least one second knob to actuate the at least one movement mechanism 140, 340, 542, 640 to move the first side of the moveable member 130, 330, 530, 630 in a vertical direction relative to the body member 110, 310, 510, 610.

The tool may include a handle, an insertion end, at least one tube extending distally away from the handle and connecting the handle and the insertion end, a securement mechanism coupled to the handle, extending through the at least one tube and protruding from the insertion end, at least one adjustment mechanism coupled to the handle, extending through the at least one tube and protruding from the insertion end, a first knob for actuating the securement mechanism, and at least one second knob for actuating the at least one adjustment mechanism.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. An interbody system, comprising:
  a device tool, comprising:
    a handle;
    a device end;
    a housing connecting the handle and the device end;
    a securement mechanism coupled to the handle, extending through the housing and protruding from the device end;
    at least one adjustment mechanism coupled to the handle, extending through the housing and protruding from the device end;
    a first knob for actuating the securement mechanism; and
    at least one second knob for actuating the at least one adjustment mechanism; and
  an interbody device, comprising:
    a first member comprising an interior surface, an outer surface configured to engage a first vertebral body;
    a second member pivotably coupled with the first member by a hinge, the second member comprising an interior surface, an outer surface configured to engage a second vertebral body, a tool attachment opening for receiving the securement mechanism of the device tool, and at least one adjustment opening adjacent the tool attachment opening configured to receive the at least one adjustment mechanism; and
at least one movement mechanism extending between the interior surfaces of the first and second members configured to selectively adjust the relative orientation of the first and second members,
wherein the at least one adjustment mechanism of the device tool is configured to actuate the at least one movement mechanism of the interbody device by operation of the at least one second knob when the at least one adjustment mechanism is positioned within the at least one adjustment opening and operatively coupled with the at least one movement mechanism; and
wherein the at least one movement mechanism is configured such that actuation of the at least one movement mechanism by the at least one adjustment mechanism by operation of the at least one second knob adjusts a height of the at least one movement mechanism.

2. The system of claim 1, wherein the second member further comprises an alignment opening, and wherein the device tool further comprises an alignment protrusion extending from the device end, the alignment protrusion being configured to mate within the alignment opening.

3. The system of claim 2, wherein the alignment opening and the alignment protrusion define corresponding non-circular cross-sectional shapes.

4. The system of claim 2, wherein the tool attachment opening extends from the alignment opening, and wherein securement mechanism extends through and from the alignment protrusion.

5. The system of claim 4, wherein the tool attachment opening comprises internal threads, and the securement mechanism comprises external threads configured to threadably engage with the internal threads of the tool attachment opening by operation of the first knob when the alignment protrusion is mated within the alignment opening to selectively secure the interbody device to the device end of the device tool.

6. The system of claim 1, wherein the tool attachment opening comprises internal threads, and the securement mechanism comprises external threads configured to threadably engage with the internal threads of the tool attachment opening by operation of the first knob to selectively secure the interbody device to the device end of the device tool.

7. The interbody system of claim 1, wherein the at least one adjustment mechanism of the device tool comprises two adjustment mechanisms actuated by the at least one second knob.

8. The interbody system of claim 7, wherein the securement mechanism is positioned between the two adjustment mechanisms at the device end of the device tool.

9. The interbody system of claim 7, wherein the at least one adjustment opening of the second member of the interbody device comprises two adjustment openings, and the at least one movement mechanism comprises two movement mechanisms, and wherein a first adjustment mechanism of the two adjustment mechanisms is configured to actuate a first movement mechanism of the two movement mechanisms by operation of the at least one second knob when the first adjustment mechanism is positioned within a first adjustment opening of the two adjustment openings and operatively coupled with the first movement mechanism, and a second adjustment mechanism of the two adjustment mechanisms is configured to actuate a second movement mechanism of the two movement mechanisms by operation of the at least one second knob when the second adjustment mechanism is positioned within a second adjustment opening of the two adjustment openings and operatively coupled with the second movement mechanism.

10. The interbody system of claim 9, wherein the at least one second knob comprises a singular second knob.

11. The interbody system of claim 1, wherein the hinge comprises at least one of a pivot cylinder and a hinge channel of the first member and at least one of a pivot cylinder and a hinge channel of the second member, wherein the at least one pivot cylinder or hinge channel of the first member engages the at least one hinge channel or pivot cylinder, respectively, of the second member.

12. The interbody system of claim 1, wherein the at least one second knob is positioned at a distal end of the handle that is distal to the housing, and the first knob is positioned at a proximal end of the handle that is proximal to the housing.

13. The interbody system of claim 1, wherein the housing defines at least one tube through which the securement mechanism and the at least one adjustment mechanism extend, and wherein the at least one tube comprises a first tube through which the securement mechanism extends and at least one second tube through which the at least one adjustment mechanism extends.

14. The interbody system of claim 1, wherein the tool attachment opening and the at least one adjustment opening are positioned in a lateral side of the second member that extends between the outer and interior surfaces thereof.

15. The interbody system of claim 1, wherein the at least one movement mechanism comprises at least one expansion assembly and at least one drive rod that adjusts the height of the at least one expansion assembly by rotation thereof, the at least one drive rod comprising a drive head aligned with the at least one adjustment opening of the second member and configured to mate with the at least one adjustment mechanism such that operation of the at least one second knob rotates the at least one adjustment mechanism and the at least one drive rod.

16. The interbody system of claim 15, wherein the at least one expansion assembly comprises a gear, a threaded rod engaged with the gear, and a load head engaged with the threaded rod, wherein the gear comprises a plurality of depressions in an exterior surface thereof and a plurality of threads on an interior surface, wherein the threaded rod comprises a plurality of threads on an exterior surface thereof that engage the plurality of threads on the interior surface of the gear and a pivot projection on a superior end, and wherein the load head comprises a top surface that engages the interior surface of the first member and a channel positioned on a bottom surface thereof that receives the pivot projection of the threaded rod therein and prevents rotation of the threaded rod.

17. The interbody system of claim 16, wherein the at least one drive rod comprises external threads that engage the plurality of depressions of the gear of the at least one expansion assembly such that rotation of the at least one drive rod rotates the gear and, thereby, translates the threaded rod with respect to the gear.

18. The interbody system of claim 15, wherein the at least one movement mechanism comprises two expansion assemblies and at least one drive rod that adjusts the total height of the two expansion assembles via assemblies by rotation thereof.

19. An interbody system, comprising:
a device tool, comprising:
a handle;
a device end;

a housing connecting the handle and the device end;
a securement mechanism coupled to the handle, extending through the housing and protruding from the device end;
at least one adjustment mechanism coupled to the handle, extending through the housing and protruding from the device end;
a first knob for actuating the securement mechanism; and
at least one second knob for actuating the at least one adjustment mechanism; and
an interbody device, comprising:
a first member comprising an interior surface, an outer surface configured to engage a first vertebral body;
a second member pivotably coupled with the first member by a hinge, the second member comprising an interior surface, an outer surface configured to engage a second vertebral body, a tool attachment opening for receiving the securement mechanism of the device tool, and at least one adjustment opening adjacent the tool attachment opening configured to receive the at least one adjustment mechanism; and
at least one movement mechanism extending between the interior surfaces of the first and second members configured to selectively adjust the relative orientation of the first and second members,
wherein the at least one adjustment mechanism of the device tool is configured to actuate the at least one movement mechanism of the interbody device by operation of the at least one second knob when the at least one adjustment mechanism is positioned within the at least one adjustment opening and operatively coupled with the at least one movement mechanism, and wherein the at least one adjustment mechanism of the device tool comprises two adjustment mechanisms actuated by the at least one second knob.

20. An interbody system, comprising:
a device tool, comprising:
a handle;
a device end;
a housing connecting the handle and the device end;
a securement mechanism coupled to the handle, extending through the housing and protruding from the device end;
at least one adjustment mechanism coupled to the handle, extending through the housing and protruding from the device end;
a first knob for actuating the securement mechanism; and
at least one second knob for actuating the at least one adjustment mechanism; and
an interbody device, comprising:
a first member comprising an interior surface, an outer surface configured to engage a first vertebral body;
a second member pivotably coupled with the first member by a hinge, the second member comprising an interior surface, an outer surface configured to engage a second vertebral body, a tool attachment opening for receiving the securement mechanism of the device tool, and at least one adjustment opening adjacent the tool attachment opening configured to receive the at least one adjustment mechanism; and
at least one movement mechanism extending between the interior surfaces of the first and second members configured to selectively adjust the relative orientation of the first and second members,
wherein the at least one adjustment mechanism of the device tool is configured to actuate the at least one movement mechanism of the interbody device by operation of the at least one second knob when the at least one adjustment mechanism is positioned within the at least one adjustment opening and operatively coupled with the at least one movement mechanism; and
wherein the housing defines at least one tube through which the securement mechanism and the at least one adjustment mechanism extend, and wherein the at least one tube is a first tube through which the securement mechanism extends and at least one second tube through which the at least one adjustment mechanism extends.

* * * * *